United States Patent [19]

Masuya et al.

[11] Patent Number: 5,534,639
[45] Date of Patent: Jul. 9, 1996

[54] HYDROQUINONE DERIVATIVES AND INTERMEDIATES FOR PRODUCTION THEREOF

[75] Inventors: Hirotomo Masuya, Inagawa-cho; Masayoshi Yamaoka, Toyonaka, both of Japan

[73] Assignee: Takeda Chemical Industries, Ltd., Osaka, Japan

[21] Appl. No.: 427,585

[22] Filed: Apr. 24, 1995

Related U.S. Application Data

[62] Division of Ser. No. 30,880, Mar. 12, 1993, Pat. No. 5,436,359.

[30] Foreign Application Priority Data

Mar. 13, 1992 [JP] Japan .................................. 4-055007

[51] Int. Cl.[6] .................. C07D 333/06; C07D 333/12
[52] U.S. Cl. ........................ 549/62; 549/76; 549/77; 549/78; 549/79; 549/80; 549/81; 549/83
[58] Field of Search ................... 549/62, 76, 77, 549/78, 79, 80, 81, 83

[56] References Cited

U.S. PATENT DOCUMENTS

| | | | |
|---|---|---|---|
| 4,271,083 | 6/1981 | Morimoto et al. | 260/396 R |
| 4,393,075 | 7/1983 | Terao et al. | 424/304 |
| 4,436,753 | 3/1984 | Imada et al. | 424/331 |
| 4,489,096 | 12/1984 | Terao et al. | 424/317 |
| 4,559,177 | 12/1985 | Okutani et al. | 260/396 R |
| 4,576,760 | 3/1986 | Imada | 558/37 |
| 4,851,413 | 7/1989 | Terao et al. | 541/277 |
| 5,180,742 | 1/1993 | Terao et al. | 514/558 |
| 5,436,359 | 7/1995 | Masuya et al. | |

OTHER PUBLICATIONS

Stern et al., J. Org. Chem., 52, pp. 2763–2768 (1987).

*Primary Examiner*—Johann Richter
*Assistant Examiner*—John Peabody
*Attorney, Agent, or Firm*—Wenderoth, Lind & Ponack

[57] ABSTRACT

There are disclosed novel hydroquinone derivatives of the formulas:

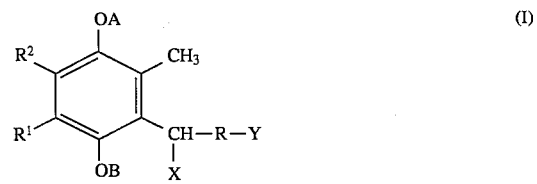

and

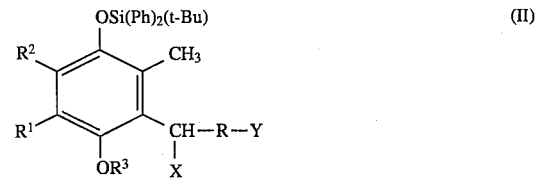

The derivatives of the formula (I) have various pharmacological activities such as antioxidation in living bodies and are useful as medicaments, and the derivatives of the formula (II) are intermediates for the production thereof.

4 Claims, No Drawings

HYDROQUINONE DERIVATIVES AND INTERMEDIATES FOR PRODUCTION THEREOF

This application is a division of application Ser. No. 08/030,880, filed Mar. 12, 1993 (now U.S. Pat. No. 5,436,359).

FIELD OF THE INVENTION

The present invention relates to novel hydroquinone derivatives which have various pharmacological activities such as antioxidation in living bodies and are useful as medicaments, and intermediates for the production thereof.

BACKGROUND OF THE INVENTION

The present inventors have studied the chemical modification of hydroquinone compounds which can readily be obtained from quinone compounds in order to solubilize in water various biologically active quinone compounds useful as medicaments, to convert them into prodrugs or to find novel pharmacological activities of these derivatives themselves.

However, in general, it is difficult to chemically modify the hydroxy group of hydroquinone compounds regioselectively at any desired site. Thus, means to synthesize their various derivatives regioselectively is required.

OBJECTS OF THE INVENTION

Under these circumstances, the present inventors have intensively studied the regioselective introduction of a protecting group into the hydroxyl group of hydroquinone derivatives, selected silyl derivatives as a protecting group which can be removed under mild conditions and examined the utilization of various silylating agents in consideration of the steric hindrance between reaction substrates and silyl groups to be introduced. As a result, it has been found that (1) the tert-butyldiphenylsilyl group is introduced into the less hindered hydroxyl group of hydroquinone derivatives in high selectivity, and (2) by using compounds obtained by introducing an appropriate protecting group into the compounds or free hydroxyl group of the compounds followed by removal of the tert-butyldiphenylsilyl group, any desired hydroxyl group of hydroquinone derivatives can be chemically-modified regioselectively. Thus, the present invention has been completed.

One object of the present invention is to provide novel hydroquinone derivatives useful as medicaments wherein any desired hydroxyl in the benzene ring is chemically modified regioselectively.

Another object of the present invention is to provide novel hydroquinone compounds wherein the hydroxyl at the 4-position is protected regioselectively. These compounds are useful as intermediates for the production of the above hydroquinone derivatives.

These objects as well as other objects and advantages of the present invention will become apparent to those skilled in the art from the following description.

SUMMARY OF THE INVENTION

According to the present invention, there are provided:
(1) A hydroquinone derivative of the formula (I):

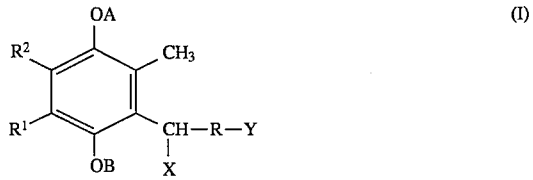

wherein $R^1$ and $R^2$ are the same or different and are methyl or methoxy, or $R^1$ and $R^2$ are joined together to form the group of the formula: —CH=CH—CH=CH—; one of A and B is optionally substituted alkyl, acyl, alkoxycarbonyl, optionally O-acylated and/or optionally esterified glycosyl, sulfo or phosphono, and the other is hydrogen; X is hydrogen, aryl or heterocyclic group; R is saturated or unsaturated bivalent straight-chain hydrocarbon group having 1 to 20 carbon atoms or a chemical bond, provided that, when X is hydrogen, R is a saturated or unsaturated bivalent straight-chain hydrocarbon group having 1 to 20 carbon atoms; and Y is hydrogen, optionally esterified or optionally amidated carboxyl or optionally substituted hydroxymethyl, provided that, when X is hydrogen and one of A and B is sulfo, Y is hydrogen and, when X is hydrogen and one of A and B is optionally O-acylated and/or optionally esterified glycosyl, Y is hydrogen or optionally substituted hydroxymethyl; and a pharmaceutically acceptable salt, and (2) A compound of the formula (II):

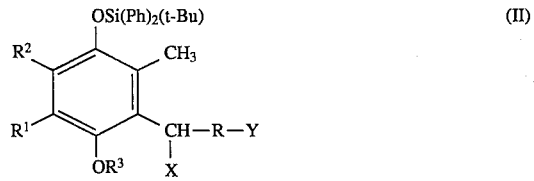

wherein $R^1$ and $R^2$ are the same or different and are hydrogen, methyl or methoxy, or $R^1$ and $R^2$ are joined together to form the group of the formula: —CH=CH—CH=CH—; $R^3$ is hydrogen or a protecting group other than silyl; X is hydrogen, aryl or heterocyclic group; R is a saturated or unsaturated bivalent straight-chain hydrocarbon group having 1 to 20 carbon atoms or a chemical bond; Y is hydrogen, optionally substituted hydroxymethyl or optionally esterified or optionally amidated carboxyl; Ph is phenyl; and t-Bu is tert-butyl.

As examples of the optionally substituted alkyl represented by A or B in the above formulas (I) and (II), there are lower alkyl having 1 to 4 carbon atoms such as methyl, ethyl, propyl, butyl or the like; carboxymethyl; pyridylmethyl; and benzyl.

Examples of the acyl represented by A or B include aliphatic acyl having 1 to 4 carbon atoms such as formyl, acetyl, propionyl or butyryl; aromatic acyl such as benzoyl, picolinoyl, nicotinoyl, isonicotinoyl or the like; glycyl; β-aspartyl; γ-glutamyl and 3-carboxypropionyl.

Examples of the alkoxycarbonyl include that having 2 to 5 carbon atoms such as methoxycarbonyl, ethoxycarbonyl, isopropoxycarbonyl, isobutoxycarbonyl, t-butoxycarbonyl or the like.

Examples of the glycosyl represented by A or B include glucosyl, rhamnosyl, sucrosyl, glucuronosyl and the like. When the hydroxy of these saccharides is O-acylated, examples of the acyl include aliphatic acyl such as acetyl; and aromatic acyl such as benzoyl, p-methylbenzoyl and nicotinoyl. When the carboxy of the saccharide residues is esterified, alkyl esters are preferred. Examples of the alkyl include that having 1 to 4 carbon atoms such as methyl, ethyl, propyl or butyl.

Examples of the aryl represented by X include phenyl, naphthyl and the like. The aryl may have one or more substituents at any position on the ring. Examples of the substituent include alkyl having 1 to 3 carbon atoms such as methyl, ethyl or the like; alkoxy having 1 to 3 carbon atoms such as methoxy, ethoxy or the like; halogen atoms such as chlorine, fluorine, bromine or the like; and the like.

As examples of the heterocyclic group represented by X, there are 5 or 6 membered rings containing, as an atom constituting the ring, one or more hetero atoms selected from oxygen, sulfur and nitrogen. Examples of the heterocyclic group include aromatic heterocyclic groups such as thienyl, furyl, pyridyl, thiazolyl, imidazolyl, triazolyl, tetrazolyl or the like; and saturated heterocyclic groups such as morpholino, thiomorpholino, piperidino, pyrrolidino, piperazino or the like. These groups may have one or more substituents at any position on the ring. Examples of the substituent include alkyl having 1 to 3 carbon atoms such as methyl, ethyl or the like; alkoxy having 1 to 3 carbon atoms such as methoxy, ethoxy or the like; halogen atoms such as chlorine, fluorine, bromine or the like; and the like.

As examples of the optionally substituted hydroxymethyl represented by Y, there are unsubstituted hydroxymethyl, methoxymethyloxymethyl, acetoxymethyl, nitroxymethyl, aminocarbonyloxymethyl, substituted aminocarbonyloxymethyl (e.g., methylaminocarbonyloxymethyl, ethylaminocarbonyloxymethyl, dimethylaminocarbonyloxymethyl, phenylaminocarbonyloxymethyl, etc.), cyclic aminocarbonyloxymethyl (e.g., morpholinocarbonyloxymethyl, piperidinocarbonyloxymethyl, etc.) and the like.

Examples of the optionally esterified carboxyl represented by Y include alkoxycarbonyl having 2 to 5 carbon atoms such as methoxycarbonyl, ethoxycarbonyl, propoxycarbonyl, butoxycarbonyl or the like; aryloxycarbonyl having 7 to 8 carbon atoms such as phenoxycarbonyl or the like.

The optionally amidated carboxyl represented by Y may be substituted aminocarbonyl whose amino group is substituted or may be cyclic aminocarbonyl. As examples of the substituent of the amino group of the substituted aminocarbonyl, there are alkyl having 1 to 4 carbon atoms such as methyl, ethyl, propyl, butyl or the like; aryl having 6 to 10 carbon atoms such as phenyl, naphthyl or the like (these may further have one or more substituents such as hydroxyl, amino, nitro, halogen, methyl, methoxy or the like at any position on the ring); hydroxyl and the like. Examples of the amidated carboxyl include aminocarbonyl, mono- or dialkylaminocarbonyl having 2 to 4 carbon atoms (e.g., methylaminocarbonyl, ethylaminocarbonyl, isopropylaminocarbonyl, dimethylaminocarbonyl, etc.), phenylaminocarbonyl, substituted phenylaminocarbonyl (e.g., p-hydroxyphenylaminocarbonyl, p-methoxyphenylaminocarbonyl, m-chlorophenylaminocarbonyl, etc.), diphenylaminocarbonyl, hydroxyaminocarbonyl, N-hydroxy-N-methylaminocarbonyl, N-hydroxy-N-phenylaminocarbonyl and the like. Examples of the cyclic aminocarbonyl include morpholinocarbonyl, thiomorpholinocarbonyl, piperidinocarbonyl or the like.

As examples of the saturated or unsaturated bivalent straight-chain hydrocarbon group having 1 to 20 carbon atoms represented by R, there are pentamethylene, hexamethylene, heptamethylene, octamethylene, deca-1,6 -diynylene or the like.

The protecting group of hydroxy other than silyl represented by $R^3$ in the formula (II) is not specifically limited so long as it has reactivities different from those of silyl, and there can be used any protecting group generally used in the field of organic synthesis. Examples thereof include lower aliphatic acyl such as acetyl, propionyl or butyryl; aromatic acyl such as benzoyl or nicotinoyl; lower alkoxymethyl such as tetrahydropyranyl, methoxymethyl, ethoxyethyl, methoxyethoxymethyl or the like; lower alkylthiomethyl such as methylthiomethyl; arylmethyl such as trityl and the like.

As examples of the pharmaceutically acceptable salt of the compound of the formula (I), there are salts with alkaline metal such as sodium, potassium or the like; salts with aluminum; salts with zinc; salts with ammonium; and salts with organic amines.

Both $R^1$ and $R^2$ in the formula (I) are preferably methyl or both are preferably methoxy. One of A and B in the formula (I) is preferably phosphono, acyl, sulfo, or optionally O-acylated and/or optionally esterified glycosyl. X in the formula (I) is preferably hydrogen or optionally substituted phenyl. R in the formula (I) is preferably a saturated or unsaturated bivalent straight-chain hydrocarbon group having 5 to 8 carbon atoms. Y in the formula (I) is preferably hydroxymethyl, or optionally esterified or optionally amidated carboxyl.

In particular, the compounds of the formula (I) wherein both $R^1$ and $R^2$ are methyl, X is phenyl, and Y is an optionally esterified or optionally amidated carboxyl, preferably unsubstituted carboxyl; and wherein both $R^1$ and $R^2$ are methoxy, X is hydrogen, and Y is an optionally substituted hydroxymethyl, preferably unsubstituted hydroxymethyl are preferable.

Preferred examples of the compound of the formula (I) include:

2,3-Dimethoxy-4-hydroxy-6-(10-hydroxydecyl)-5 -methylphenyl-1-phosphate;

2,3-Dimethoxy-4-hydroxy-6-(10-hydroxydecyl)-5 -methylphenyl-4-phosphate;

2,3-Dimethoxy-4-hydroxy-6-(10-hydroxydecyl)-5 -methyl-1-(N-methyl-1,4-dihydropyridin-3-ylcarbonyloxy)benzene;

6-(6-Carboxy-1-phenylhexyl)-4-hydroxy-2,3,5 -trimethylphenyl-1-O-β-D-glucopyranosiduronate;

6-(6-Carboxy-1-phenylhexyl)-1-hydroxy-2,3,5 -trimethylphenyl-4-sulfate; and 6-(6-Carboxy-1-phenylhexyl)-1-hydroxy-2,3,5 -trimethylphenyl-4-O-β-D-glucopyranosiduronate.

$R^1$ and $R^2$ in the formula (II) are preferably methyl or methoxy. X in the formula (II) is preferably hydrogen or optionally substituted phenyl. R in the formula (II) is preferably a saturated or unsaturated bivalent straight-chain hydrocarbon group having 5 to 8 carbon atoms. Y in the formula (II) is preferably hydroxymethyl, or optionally esterified or optionally amidated carboxyl.

In particular, the compound of the formula (II) wherein both $R^1$ and $R^2$ are methyl, X is phenyl, and Y is optionally esterified of optionally amidated carboxyl is preferable.

Preferred examples of the compound of the formula (II) include:

6-(10-Acetoxydecyl)-4-tert-butyldiphenylsilyloxy-2,3-dimethoxy-5-methylphenol;

4-tert-Butyldiphenylsilyloxy-2,3-dimethoxy-5 -methyl-6-(10-trityloxydecyl)phenol; and 4-tert-Butyldiphenylsilyloxy-1-hydroxy-6-(6 -methoxycarbonyl-1-phenylhexyl)-2,3,5-trimethylbenzene.

The compound of the formula (II) of the present invention which is an important synthetic intermediate can be obtained by introducing tert-butyldiphenylsilyl into the corresponding hydroquinone derivative of the formula (III):

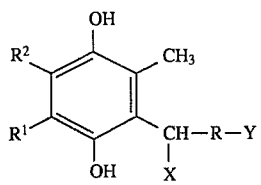

(III)

wherein each symbol is as defined above, according to the method of E. J. Corey et al. (J. Am. Chem. Soc., 94, 6190, 1972). Namely, the hydroquinone derivative of the formula (III) is reacted with imidazole and tert-butyldiphenylsilyl chloride in an amount of 1 to 3 equivalents, preferably 1.5 to 2 equivalents in an inert solvent such as dioxane, tetrahydrofuran, chloroform, dichloromethane, 1,2-dichloroethane, dimethylformamide or the like, preferably in dichloromethane The reaction temperature is 0° C. to 80° C. preferably 40° C. The reaction time is 2 to 20 hours. In this case, tert-butyldiphenylsilyl is introduced preferentially into the less hindered hydroxyl at the 4 -position in high selectivity of 96:4. The remainder being 4% is introduced into the 1-position. However, since it can be converted to the corresponding 1,4-disilyl derivative with the excess silylating agent, it can be separated readily by conventional separation methods such as column chromatography on silica gel or the like. For example, the regioselectivities of other silylating agents preferentially introduced into the 4-position are as follows: triphenylsilyl (7:5), tert-butyldimethylsilyl (3:1), triisopropylsilyl (3:1), dimethylthexylsilyl (i.e. dimethyl(1, 1,2 -trimethylpropyl)silyl) (4:1).

The 4-tert-butyldiphenylsilyl derivative of the hydroquinone compound thus obtained can be subjected to alkylation, acylation, glycosylation, sulfation or phosphorylation followed by removal of the tert-butyldiphenylsilyl at the 4-position to obtain the corresponding 1-derivative as shown in Scheme 1. Further, an appropriate protecting group is introduced into the hydroxyl at the 1 -position of the synthetic intermediate of the formula (II) wherein $R^3$ is hydrogen, then the tert-butyldiphenylsilyl at the 4-position is removed and the hydroxyl at the 4-position is alkylated, acylated, glycosylated, sulfated or phosphorylated followed by removal of the protecting group of the hydroxyl at the 1-position to obtain the corresponding 4-derivative.

Scheme 1

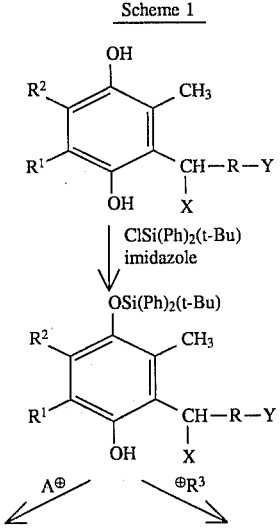

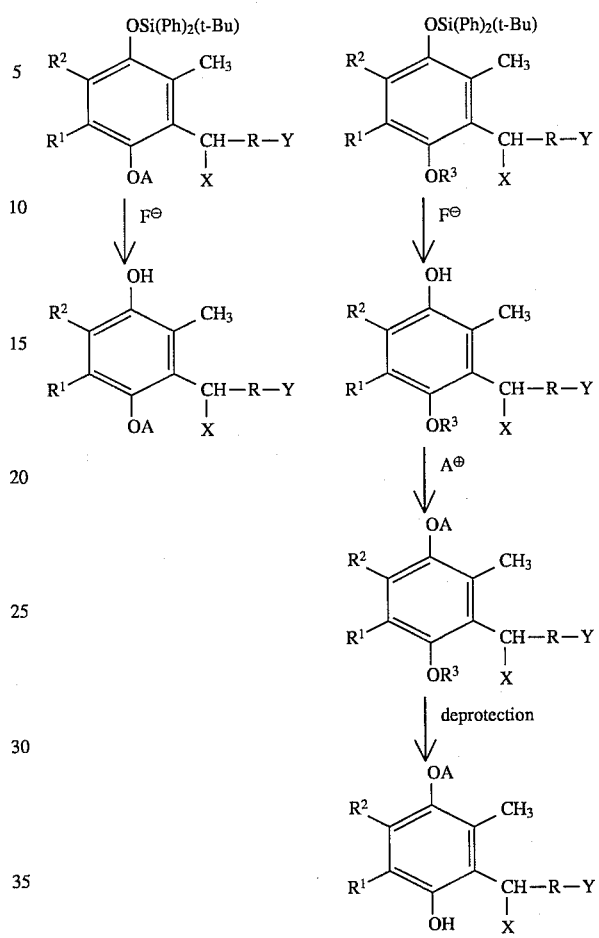

wherein each symbol is as defined above.

The alkyl derivative of hydroquinone of the above formula (I) of the present invention can be obtained by subjecting the synthetic intermediate of the formula (II) to alkylation followed by desilylation, or by protecting the synthetic intermediate of the formula (II) with lower aliphatic acyl such as acetyl followed by desilylation, alkylation and then deacylation to give the corresponding 1- or 4-alkyl derivative, regioselectively. The alkylation can be carried out in an inert solvent by using a lower aklyl halide and tertiary organic amine and the like according to conventional methods.

The acyl derivative of hydroquinone of the above formula (I) can be obtained by subjecting the synthetic intermediate of the formula (II) to desilylation followed by acylation, or by introducing a protecting group readily removable such as methoxyethoxymethyl into the synthetic intermediate of the formula (II) followed by desilylation, acylation and then deprotection to give the corresponding 1- or 4-acyl derivative, regioselectively.

The acylation can be carried out in an inert solvent according to conventional methods by using an acyl halide, an acid anhydride or the like together with a tertiary organic amine, or a carboxylic acid derivative activated by acylimidazole such as 1,1'-carbonyldiimidazole.

The hydroquinone glycosyl derivative of the formula (I) of the present invention can be prepared by reacting the synthetic intermediate of the formula (II) with O-glycosyl-trichloroacetimidate of the formula (IV):

Gly—X  (IV)

wherein Gly is the above O-acylated and/or esterified glycosyl residue and X is trichloroacetimidoyl (when R³ of the synthetic intermediate of the formula (II) is a protecting group, this reaction is carried out after desilylation) according to a per se known method (R. R. Schmidt), Angew. Chem. Int. Ed. Engl., 25, 212 (1986)) followed by deprotection. As the O-acyl group in the compound (IV), lower aliphatic acyl such as acetyl is preferred. As the ester group, lower alkyl such as methyl is preferred. Examples of the compound (IV) include O-acetyl-α-glycopyranosyltrichloroacetimidate, O-acetyl-α-galactopyranosyltrichloroacetimidate and O-acetyl-α-mannopyranosyltrichloroacetimidate described in the above paper and methyl 2,3,4-tri-O-acetyl-1-O-(trichloroacetimidoyl)-α-D-glycopyranuronate (B. Fischer et al., J. Org. Chem., 49, 4988 (1984)).

In this reaction, a Lewis acid is used as a catalyst in an inert solvent. As the Lewis acid to prevent the production of the corresponding α-anomer as a by-product, boron trifluoride diethyl ether complex or trimethylsilyl trifluoromethanesulfonate is preferred. As the inert solvent, dichloromethane, dichloroethane, chloroform, acetonitrile or propionitrile is preferred. The reaction temperature is −78° C. to 0° C. The reaction time is 15 to 60 minutes. The amount of the trichloroacetimidoyl derivative (IV) to be used is 1.0 to 1.2 equivalents based on the hydroquinone derivative (II) either hydroxyl of which is protected.

After completion of the reaction, the reaction mixture is subjected to solvent extraction and per se known separation and purification methods such as chromatography, recrystallization and the like to obtain the 1- or 4 -glycosyl derivative in any desired purity. Alternatively, the reaction mixture can be subjected to deprotection without such separation and purification.

The sulfo derivative of the hydroquinone of the above formula (I) of the present invention can be obtained by reacting the synthetic intermediate of the formula (II) with a reactive derivative of sulfuric anhydride, for example. When R³ of the synthetic intermediate of the formula (II) is a protecting group, this reaction is carried out after desilylation.

Examples of the above reactive derivative of sulfuric anhydride include complexes such as sulfur trioxide-pyridine, sulfur trioxide-dioxane, sulfur trioxidetrimethylamine, sulfur trioxide-dimethylformamide or the like. In addition, sulfuric anhydride, sulfuric-chlorosulfonic acid can also be used.

As the solvent in this reaction, an inert solvent is preferably used. Examples thereof include dioxane, tetrahydrofuran, chloroform, dichloromethane, pyridine, dimethylformamide and the like.

The amount of the reactive derivative of sulfuric anhydride to be used is preferably 1.0 to 5.0 mole per 1 mole of the corresponding hydroquinone derivative. In this case, the reaction temperature is preferably 0° C. to 40° C.

After completion of the reaction, the reaction mixture is subjected to solvent extraction and per se known separation and purification methods such as chromatography, recrystallization and the like to obtain the 1- or 4-sulfate (salt) in any desired purity. Alternatively, the reaction mixture can be subjected to deprotection without such separation and purification.

The phosphono derivative of the formula (I) can be obtained by reacting the synthetic intermediate of the formula (II) with an appropriate phosphorylating agent. When R³ of the synthetic intermediate of the formula (II) is a protecting group, the reaction is carried out after desilylation.

Examples of the phosphorylating agent to be used in the above reaction include orthophosphoric anhydride, metaphosphoric acid, phosphorus pentachloride, phosphorus oxychloride, pyrophosphoryl tetrachloride, tetra-p-nitrophenylpyrophosphoric acid, dimorpholylphosphoryl bromide, o-phenylene phosphoryl chloride, diphenylphosphoryl chloride, di-p-nitrobenzylphosphoryl chloride and the like. The phosphorylating agent can be used alone or in combination with about 1 to 5 equivalents of a base in a solvent.

Examples of the base include organic bases such as pyridine, 2,6-lutidine, picoline, triethylamine, N-methylmorpholine or the like; inorganic bases such as sodium hydroxide, potassium hydroxide, sodium bicarbonate, sodium carbonate or the like; and the like.

Examples of the solvent include water, acetone, acetonitrile, dioxane, N,N-dimethylformamide, tetrahydrofuran, dichloromethane and the like. These solvents can be used alone or in combination thereof.

The amount of the phosphorylating agent to be used is preferably 1.0 to 5.0 mol per 1 mol of the corresponding hydroquinone derivative. The reaction temperature is preferably −20° C. to 40° C.

After completion of the reaction, the reaction mixture is subjected to solvent extraction and per se known separation and purification methods such as chromtography, recrystallization and the like to obtain the 1- or 4 -phosphate (salt) in any desired purity. Alternatively, the reaction mixture can be subjected to deprotection without such separation and purification.

The hydroquinone derivative thus obtained can be subjected to deprotection, if necessary.

When the hydroquinone has tert-butyldiphenylsilyloxy at the 4-position, the silyl group can be removed by per se known methods such as (1) reaction with tetra-n-butylammonium fluoride in tetrahydrofuran or reaction in acetic acid-water (J. Am. Chem. Soc., 94, 6190 (1972)), (2) reaction with hydrofluoric acid in anhydrous acetonitrile (Tetrahedron Lett., 1979, 3981), (3) reaction with N-bromosuccinimide in dimethyl sulfoxide (Synthesis, 1980, 234), (4) reaction with lithium tetrafluoroborate (Tetrahedron Lett., 21, 35 (1980)), (5) reaction with an aqueous solution of hydrogen chloride (Tetrahedron Lett., 24, 3251 (1983)) or the like. Alternatively, the removal can be carried out under conditions for the hydrolysis of ester and acyl groups used in the present invention. Namely, the silyl group, ester group and acyl group can be removed simultaneously by reaction with excess 2N-sodium hydroxide solution in a mixed solvent of water-methanol-tetrahydrofuran at room temperature for 15 hours.

When the hydroxyl group at the 1-position of the hydroquinone is protected by R³ which is lower aliphatic acyl or aromatic acyl such as acetyl or benzoyl, R³ can be removed by alkaline hydrolysis according to conventional methods. When R³ is methoxymethyl, methoxyethoxymethyl, methylthiomethyl or the like which forms a ether bond, it can be removed by per se known methods such as hydrochloric acid-tetrahydrofuran method (Tetrahedron Lett., 1976, 809), zinc bromide or titanium tetrachloride method (Tetrahedron Lett., 1976, 809), the method using $Hg^{++}$ or $Ag^{++}$ (Tetrahedron Lett., 1975, 3269), bromodimethylborane or bromodiphenylborane method (Tetrahedron Lett., 24, 3969 (1983)) or the like.

When either A or B of the compound of the formula (I) is protected phosphono, the deprotection can be carried out by per se known methods such as hydrolysis with an acid, catalytic reduction or the like. When either A or B of the compound of the formula (I) is O-acylated and/or esterified glycosyl, it can be removed by conventional methods such as alkaline hydrolysis or the like.

When the compound (I) thus obtained is in the form of a salt, it can be converted to its free acid, if necessary. When it is a free acid, it can be converted to its salt by adding a base.

Further, the desired compound (I) can be separated and purified by known methods such as extraction, concentration, crystallization, recrystallization, chromatography and the like.

The compound (I) of the present invention itself has various biological activities against animals, particularly mammals (e.g., mouse, rat, guinea pig, dog, rabbit, human, etc.) based mainly on inhibitory activity of fatty acid peroxide formation such as hypotensive activity, antiallergic activity, antiulcer activity, antiinflammtory activity, analgesic activity, antiasthmatic activity, immunomodulatory activity, diuretic activity, platelet aggregation inhibitory activity, ameliorative activity of brain and circulatory organs and the like. The compound (I) are useful as medicaments such as hypotensive agents, analgesics, antiulcer agents, antiinflammatory agents, diuretics, antiallergic agents, immunomodulators, antithrombogenic agents, ameliorative agents for brain and circulatory organs and the like for treatment or prevention of, for example, hypertension, cerebral thrombosis, ischemic cardiac infarction, coronary vascular disorders, incontinence of regulation of prostaglandin or thromboxane biosynthesis, immunodeficiency, atherosclerosis, allergosis, bronchial asthma and the like.

The compounds of the present inventions have low toxicity, and can safely be administered orally or parenterally as it is or in combination with a per se known pharmacologically acceptable carrier or excipient as a pharmaceutical composition (e.g., tablets, capsules including soft capsules and microcapsules, liquids and solutions, injections, suppositories, etc.). The dose varies depending upon the subject to be treated, administration route, conditions to be treated. For example, when administered orally to an adult patient with hypertension or bronchial asthma, normally, the compound is preferably administered in a unit dose of about 0.2 mg/kg to about 25 mg/kg body weight 1 to 3 times a day. For a serious patient who is impossible to treat by oral administration, parenteral administration of the water-soluble derivative of the compound (I) of the present invention is especially effective.

The raw materials in the present invention, namely 2,3-dimethoxy-6-(10-hydroxydecyl)-5-methyl-1,4-benzoquinone, 6-(12-hydroxydodeca-5,10-diyn-1-yl)-2,3,5-trimethyl-1,4-benzoquinone, 6-(11-carboxyundeca-5,10-diyn-1-yl)-2,3,5-trimethyl-1,4-benzoquinone and 6-(3-pyridylmethyl)-2,3,5-trimethyl-1,4-benzoquinone can be prepared, for example, according to the methods described in JP-B 1-37384, JP-A 57-109739, JP-B 3-2133, JP-A 63-45257 or the like.

As described above, according to the present invention, there are provided novel compounds wherein the hydroxyl at the 4-position of the hydroquinone derivative is protected regioselectively. Further, by using these compounds as intermediates for the production, there are provided novel hydroquinone derivatives useful as medicaments wherein any desired hydroxyl is chemically modified, regioselectively.

The following reference examples and examples further illustrate the present invention in detail but are not to be construed to limit the scope thereof. In the number of the examples, the symbol "A" represents the production of the compounds of the above formula (I) and the symbol "B" represents the production of the compounds of the above formula (II).

REFERENCE EXAMPLE 1

6-(10-Acetoxydecyl)-2,3-dimethoxy-5-methylhydroquinone 2,3-Dimethoxy-6-(10-hydroxydecyl)-5-methyl-1,4-benzoquinone (3.38 g) was dissolved in dichloromethane (50 ml). Pyridine (1 ml) was added, and acetyl chloride (0.8 ml) was added with stirring under ice-cooling. After stirring for 1 hour at the same temperature, the mixture was washed with 0.1N hydrochloric acid (50 ml) followed by water (50 ml). The dichloromethane layer was concentrated under reduced pressure to obtain 6-(10-acetoxydecyl)-2,3-dimethoxy-5-methyl-1,4-benzoquinone as a red oil. This oil was dissolved in ether (50 ml), and a solution of sodium hydrosulfite (4 g) in water (50 ml) was added. Stirring was continued at room temperature until the red color of the ether layer disappeared. The ether layer was separated, dried over anhydrous magnesium sulfate and concentrated under reduced pressure to obtain the desired compound (3.8 g) as a pale yellow oil.

EXAMPLE B-1

6-(10-Acetoxydecyl)-4-tert-butyldipheylsilyloxy-2,3-dimethoxy-5-methylphenol 6-(10-Acetoxydecyl)-2,3-dimethoxy-5-methylhydroquinone (38.0 g) and tert-butylchlorodiphenylsilane (55.0 g) were dissolved in dichloromethane (50 ml). Imidazole (13.6 g) was added under a stream of nitrogen at room temperature. The mixture was stirred at 43° C. for 16 hours. The reaction mixture was washed with water (50 ml) and concentrated under reduced pressure. The residue was subjected to column chromatography on silica gel and eluted with hexane/ethyl acetate (7:3) to obtain the desired compound (58.0 g).

NMR (CDCl$_3$) δ (ppm): 1.05 (9H, s), 1.30 (16H, br.s), 2.04 (3H, s), 2.27 (3H, s), 2.60 (2H, t, J=7.90 Hz), 2.91 (3H, s), 3.47 (3H, s), 4.05 (2H, t, J=6.6 Hz), 5.30 (1H, s), 7.30–7.75 (10H, m).

IR (neat) v: 3540, 2925, 2860, 1740, 1465, 1430, 1380, 1260, 1240, 1190, 1115, 970, 820, 705, 610 cm$^{-1}$.

REFERENCE EXAMPLE 2

Methyl 1-O-trichloroacetimidoyl-2,3,4-tri-O-acetyl-α-D-glucopyranuronate

60% Oily sodium hydride (0.366 g) was added to an ice-cooled solution of methyl 2,3,4-tri-O-acetyl-D-glucopyranuronate (3.96 g), trichloroacetonitrile (12 ml) and dichloromethane (100 ml), and the mixture was stirred at room temperature for 15 minutes. The reaction mixture was subjected to short column (70 φ×50 mm) chromatography on silica gel and eluted with ethyl acetate/hexane (1:1). The eluate was concentrated under reduced pressure to obtain the desired compound (4.37 g) as crystals (mp: 108° C.).

EXAMPLE A-1

Methyl 1-O-[6-(10-acetoxydecyl)-4-hydroxy-2,3-dimethoxy-5-methylphenyl]-2,3,4-tri-O-acetyl-β-D-glucopyranosiduronate 6-(10-Acetoxydecyl)-4-tert-butyldiphenylsilyloxy-2,3-dimethoxy-5-methylphenol (0.62 g) and methyl 1-O-trichloroacetimidoyl-2,3,4-tri-O-acetyl-α-D-glucopyranuronate (0.82 g) were dissolved in dichloromethane (10 ml), and the solution was cooled to −10° C. Boron trifluoride diethyl ether (0.2 ml) was added with stirring. The mixture was stirred under ice-cooling for 30 minutes followed by addition of water (10 ml) containing sodium bicarbonate (1 g) and stirring. The dichloromethane layer was separated and concentrated under reduced pressure to obtain crude methyl 1-O-[6-(10-acetoxydecyl)-4-tert-butyldiphenylsilyloxy-2,3-dimethoxy-5-methylphenyl]-2,3,4-tri-O-acetyl-β-D-glucopyranosiduronate.

The crude product thus obtained was dissolved in tetrahydrofuran (10 ml), and tetrabutylammonium fluoride trihydrate (0.2 g) was added. The mixture was stirred at room temperature for 2 hours. The reaction mixture was concentrated under reduced pressure, and the residue was subjected to column chromatography on silica gel and eluted with ethyl acetate/hexane (1:1) to obtain the desired compound (0.36 g).

NMR (CDCl$_3$) δ (ppm): 1.30 (16H, br.s), 2.02 (3H, s),2.05 (3H, s), 2.10 (3H,s), 2.11 (3H, s), 2.14 (3H, s), 3.69 (3H, s), 3.79 (3H, s), 3.92 (3H, s), 4.06 (2H, t, J=6.6 Hz), 5.63 (1H, s).

EXAMPLE A-2

Sodium 1-O-[4-hydroxy-6-(10-hydroxydecyl)-2,3-dimethoxy-5-methylphenyl]-β-D-glucopyranosiduronate

Method 1

6-(10-Acetoxydecyl)-4-tert-butyldiphenylsilyloxy-2,3-dimethoxy-5-methylphenol (0.62 g) and methyl 1-O-trichloroacetimidoyl-2,3,4-tri-O-acetyl-α-D-glucopyranuronate (0.82 g) were dissolved in dichloromethane (10 ml), and the solution was cooled to −10° C. Boron trifluoride diethyl ether (0.2 ml) was added with stirring. The mixture was stirred under ice-cooling for 30 minutes followed by addition water (10 ml) containing sodium bicarbonate (1 g) and stirring. The dichloromethane layer was separated and concentrated under reduced pressure to obtain crude methyl 1-O-[6-(10-acetoxydecyl)-4-tert-butyldiphenylsilyloxy-2,3-dimethoxy-5-methylphenyl]-2,3,4-tri-O-acetyl-β-D-glucopyranosiduronate.

The crude product thus obtained was dissolved in tetrahydrofuran (10 ml), and tetrabutylammonium fluoride trihydrate (0.2 g) was added. The mixture was stirred at room temperature for 2 hours. After concentration under reduced pressure, the residue was dissolved in methanol (10 ml). A solution of sodium hydroxide (1N, 10 ml) was added under ice-cooling, and the mixture was allowed to react at room temperature for 15 hours. The reaction mixture was extracted with ether (20 ml), and the aqueous layer was concentrated under reduced pressure. The residue was subjected to Sephadex (trade mark) LH-20 column chromatography and eluted with water. The desired fraction was lyophilized to obtain the desired compound (0.47 g).

Method 2

6-(10-Acetoxydecyl)-4-tert-butyldiphenylsilyloxy-2,3-dimethoxy-5-methylphenol (0.62 g) and methyl 1-O-trichloroacetimidoyl-2,3,4-tri-O-acetyl-α-D-glucopyranuronate (0.82 g) were dissolved in dichloromethane (10 ml), and the solution was cooled to −10° C. Boron trifluoride diethyl ether (0.2 ml) was added with stirring. The mixture was stirred under ice-cooling for 30 minutes followed by addition of water (10 ml) containing sodium bicarbonate (1 g) and stirring. The dichloromethane layer was separated and concentrated under reduced pressure to obtain crude methyl 1-O-[6-(10-acetoxydecyl)-4-tert-butyldiphenylsilyloxy-2,3-dimethoxy-5-methylphenyl]-2,3,4-tri-O-acetyl-β-D-glucopyranosiduronate.

To the crude product thus obtained was added methanol (30 ml), tetrahydrofuran (10 ml) and 1N sodium hydroxide solution (15 ml). The mixture was stirred at room temperature for 24 hours. After concentration under reduced pressure, the residue was extracted with ether (20 ml). The aqueous layer was concentrated. The residue was subjected to Sephadex (trade mark) LH-20 column chromatography and eluted with water. The desired fraction was lyophilized to obtain the desired compound (0.50 g).

mp: 219°–221° C.

Elemental Analysis for $C_{25}H_{39}O_{11}Na \cdot 0.5H_2O$ Calcd.: C,54.84; H,7.36 Found: C,54.95; H,7.09

NMR (D$_2$O) δ (ppm): 1.15–1.55 (16H, m), 2.08 (3H, s), 2.65 (2H, m), 3.53 (2H, t, J=6.76 Hz), 3.82 (3H, s), 3.87 (3H, s), 4.86 (1H, d, J=7.09 Hz).

UV λmax$^{H2O}$ 200 nm E$_1$cm (1%)=848,279 nm E$_1$cm (1%)=30.

IR (KBr) v: 1610, 1460, 1420, 1300, 1100, 1050 cm$^{-1}$.

EXAMPLE A-3

Sodium 1-O-[2,3-dimethoxy-4-hydroxy-6-(10-hydroxydecyl)-5-methylphenyl]-α-D-glucopyranosiduronate 2,3-Dimethoxy-6-(10-hydroxydecyl)-5-methyl-1,4-benzoquinone (338 mg, 1 mmol) was dissolved in dichloromethane (5 ml). Pyridine (0.1 ml, 1.2 mmol) followed by acetyl chloride.(0.08 ml, 1.1 mmol) was added with stirring under ice-cooling. The mixture was stirred at the same temperature for 1 hour. Water (5 ml) was added to the reaction mixture which was then stirred at room temperature for 20 minutes. Then sodium hydrosulfite (400 mg, 2.3 mmol) was added, and the mixture was stirred for 2 hours. The dichloromethane layer was separated, dried over anhydrous magnesium sulfate and concentrated under reduced pressure. The residue was dissolved in dichloromethane (5 ml), and tert-butylchlorodiphenylsilane (550 mg, 2 mmol) was added. Then imidazole (136 mg, 2 mmol) was added under a stream of nitrogen. After stirring at 43° C. for 16 hours, the mixture was washed with water (5 ml), and the organic layer was dried over anhydrous magnesium sulfate. Concentration under reduced pressure gave crude 6-(10-acetoxydecyl)-4-tert-butyldiphenylsilyloxy-2,3-dimethoxy-5-methylphenol. The crude product was dissolved in dichloromethane (10 ml) followed by addition of methyl 1-O-trichloroacetimidoyl- 2,3,4-tri-O-acetyl-α-D-glucopyranuronate (2.1 mmol), and the mixture was ice-cooled. Boron trifluoride diethyl ether (0.2 ml) was added, and the mixture was stirred at the same temperature for 30 minutes. Then water (10 ml) containing sodium bicarbonate (1 g) was added, and the mixture was stirred for 5 minutes. The dichloromethane layer was separated and concentrated under reduced pressure. To the residue were added tetrahydrofuran (15 ml), methanol (10 ml) and 1N sodium hydroxide solution (20 ml), and the mixture was allowed to react at room temperature for 40 hours. The solvent was distilled off under reduced pressure, and the residue was extracted with ether (20 ml). Then the aqueous layer was subjected to Sephadex (trade mark) LH-20 column chromatography and eluted with water. The desired fraction was lyophilized to obtain the desired compound (290 mg).

EXAMPLE A-4

Sodium 1-O-[4-Hydroxy-6-(12-hydroxydodeca-5,10-diyn-1-yl)-2,3,5-trimethylphenyl-β-D-glucopyranosiduronate 6-(12-Hydroxydodeca-5,10-diyn-1-yl)-2,3,5 -trimethyl-1, 4-benzoquinone (326 mg, 1 mmol) was treated according to the same manner as that described in Example A-3 to obtain the desired compound (310 mg).

Elemental Analysis for $C_{27}H_{35}O_9Na·H_2O$ Calcd.: C,59.55; H,6.85 Found: C,59.40; H,6.55

NMR ($D_2O$) δ (ppm): 1.542 (4H, m), 1.651 (2H, quintet, J=7.0 Hz), 2.150 (3H, s), 2.214 (3H, s), 2.234 (3H, s), 2.260–2.350 (6H, m), 2.74 (2H, m), 2.85 (2H, m), 3.492 (1H,d, J=9.50 Hz), 3.590 (2H, m), 3.680 (1H, dd, J=7.80, 9.50 Hz), 4,171 (2H, t, J=2.20 Hz), 4.690 (1H, d, J=7.80 Hz).

IR (KBr) ν: 3380, 1600 cm$^{-1}$. SIMS ($H_2O$+Glycerol): 527 (M+1), 549 (M+Na) SIMS ($H_2O$+Glycerol+0.1NKJ): 527 (M+1), 543 (M−Na+K+1), 565 (M+K), 581 (M−Na+K+K).

EXAMPLE B-2

1-Acetoxy-6-(10-acetoxydecyl)-4-tert-butyldiphenylsilyloxy-2,3-dimethoxy-5-methylbenzene 6-(10-Acetoxydecyl)-4-tert-butyldiphenylsilyloxy-2,3-dimethoxy-5-methylphenol (0.65 g) was dissolved in dichloromethane (5 ml), and triethylamine (0.2 ml) followed by acetyl chloride (0.08 g) was added. The mixture was stirred at the same temperature for 30 minutes. The reaction mixture was concentrated, and then the residue was subjected to column chromatography on silica gel and eluted with hexane/ethyl acetate (9:1) to obtain the desired compound (0.483 g).

NMR (CDCl$_3$) δ (ppm): 1.05 (9H, s), 1.31 (16H, s), 2.05 (3H, s), 2.29 (3H, s), 2.31 (3H, s), 2.45 (2H, t, J=7.90 Hz), 2.87 (3H, s), 3.40 (3H, s), 4.06 (2H, t, J=6.6 Hz), 7.35–7.70 (10H, m).

IR (neat) ν: 2925, 2850, 1770, 1760, 1470, 1420, 1360, 1240, 1200, 1110, 1060, 1020, 960 cm$^{-1}$.

EXAMPLE A-5

1-Acetoxy-6-(10-acetoxydecyl)-2,3-dimethoxy-4-hydroxy-5-methylbenzene

1-Acetoxy-6-(10-acetoxydecyl)-4 -tert-butyldiphenylsilyloxy-2,3-dimethoxy-5-methylbenzene (0.483 g) was dissolved in tetrahydrofuran (5 ml), and tetrabutylammonium fluoride trihydrate (0.5 g) was added. The mixture was stirred at room temperature for 30 minutes. After concentration under reduced pressure, the residue was subjected to column chromatography on silica gel and eluted with hexane/ethyl acetate (7:3) to obtain the desired compound (0.24 g).

NMR (CDCl$_3$) δ (ppm): 1.29–1.60 (16H,s), 2.05 (3H,s), 2.16 (3H, s), 2.33 (3H, s), 2.43 (2H, t, J=7.90 Hz), 3.83 (3H, s), 3.91 (3H, s), 4.06 (2H, t, J=6.60 Hz), 5.73 (1H, s).

IR (neat) ν: 3450, 2925, 2850, 1760, 1740, 1490, 1465, 1425, 1380, 1365, 1240, 1210, 1110, 1050 cm$^{-1}$.

EXAMPLE A-6

Sodium 1-O-[2,3-dimethoxy-1-hydroxy-6-(10-hydroxydecyl)-5-methylphenyl]-β-D-glucopyranosiduronate 1-Acetoxy-6-(10-acetoxydecyl)-2,3-dimethoxy-4 -hydroxy-5-methylbenzene (0.9 g) and methyl 1-O-trichloroacetimidoyl-2,3,4-tri-O-acetyl-α-D-glucopyranosiduronate (1.3 g) were dissolved in dichloromethane (20 ml). Boron trifluoride diethyl ether (0.4 ml) was added with stirring under ice-cooling, and the mixture was stirred at the same temperature for 30 minutes. Then water (20 ml) containing sodium bicarbonate (1 g) was added, and the mixture was stirred for 10 minutes. The dichloromethane layer was separated and concentrated under reduced pressure to obtain crude methyl 1-O-[1-acetoxy-6-(10-acetoxydecyl)-2,3 -dimethoxy-5-methylphenyl]-2,3,4-tri-O-acetyl-β-D-glucopyranosiduronate. This was dissolved in methanol (20 ml), and 1N sodium hydroxide solution (20 ml) was added under ice-cooling. The mixture was allowed to react at room temperature for 16 hours. The methanol was distilled off under reduced pressure, and the residue was subjected to Sephadex (trade mark) LH-20 column chromatography and eluted with water. The desired fraction was lyophilized to obtain the desired compound (0.88 g). This compound was dissolved in a small amount of methanol for crystallization to obtain crystals (0.68 g).

mp. 210°–211° C.

Elemental Analysis for $C_{25}H_{39}O_{11}Na$ Calcd.: C,55.75; H,7.30 Found : C,55.48; H,7.29

NMR ($D_2O$) δ (ppm): 1.15–1.55 (16H, m), 2.20 (3H, s), 2.55 (2H, s), 3.53 (2H, t, J=6.76 Hz), 3.81 (3H, s), 3.86 (3H, s), 4.78 (1H, d, J=7.58 Hz).

IR (KBr) ν: 1610, 1460, 1425, 1370, 1300, 1090, 1060 cm$^{-1}$.

UV ν max$^H_{20}$ 200 nm, $E_1$cm (1%)=803,279 nm, $E_1$cm (1%)=28. $[\alpha]_D^{24}$=−29.8° (c=0.215, $H_2O$).

EXAMPLE A-7

Sodium 1-O-[2,3-dimethoxy-1-hydroxy-6-(10-hydroxydecyl)-5-methylphenyl]-β-D-glucopyranosiduronate 2,3-Dimethoxy-6-(10-hydroxydecyl)-5-methyl-1,4 -benzoquinone (338 mg, 1 mmol) was dissolved in dichloromethane (5 ml). Pyridine (0.1 ml, 1.2 mmol) followed by acetyl chloride (0.08 ml, 1.1 mmol) was added with stirring under ice-cooling. The mixture was stirred at the same temperature for 1 hour. Water (5 ml) was added to the reaction mixture which was then stirred at room temperature for 20 minutes. Then sodium hydrosulfite (400 mg, 2.3 mmol) was added, and the mixture was stirred for 2 hours. The dichloromethane layer was separated, dried over anhydrous magnesium sulfate and concentrated under reduced pressure. The residue was dissolved in dichloromethane (5 ml), and tert-butylchlorodiphenylsilane (550 mg, 2 mmol) was added. Then imidazole (136 mg, 2 mmol) was added under a stream of nitrogen. The reaction mixture was stirred at 43° C. for 16 hours and then washed with water (5 ml), and the organic layer was dried over anhydrous magnesium sulfate. Concentration under reduced pressure gave crude 6-(10 -acetoxydecyl)-4-tert-butyldiphenylsilyloxy-2,3-dimethoxy-5 -methylphenol. The crude product was dissolved in dichloromethane (5 ml), and pyridine (0.1 ml, 1.2 mmol) followed by acetyl chloride (0.08 ml, 1.1 mmol) was added. The mixture was stirred at the same temperature for 30 minutes and washed with water (5 ml), and the dichloromethane layer was concentrated under reduced pressure. The residue was dissolved in tetrahydrofuran (8 ml), and tetrabutylammonium fluoride trihydrate (731 mg, 2 mmol) was added. The mixture was stirred at room temperature for 30 minutes. The reaction mixture was concentrated under reduced pressure, and the residue was dissolved in ether and washed with water. The ether layer was dried over anhydrous magnesium sulfate and concentrated under reduced pressure to obtain crude 1-acetoxy-6-(10-acetoxydecyl)-2,3-dimethoxy-4-hydroxy-5-methylbenzene. This crude product was dissolved in dichloromethane (10 ml): Methyl 1-O-trichloroacetimidoyl-2,3,4-tri-O-acetyl-α-D-glucopyranosiduronate (1.4 g, 3 mmol) was added, and the mixture was ice-cooled. Boron trifluoride diethyl ether (0.2 ml) was added, and the mixture was stirred at the same temperature for 30 minutes. Then water (10 ml) containing sodium bicarbonate (1 g) was added, and the mixture was stirred for 5 minutes. The dichloromethane layer was separated and concentrated under reduced pressure to obtain crude methyl 1-O-[1-acetoxy-6-(10-acetoxydecyl)-2,3-dimethoxy-5 -methylphenyl]-2,3,4-tri-O-acetyl-β-D-glucopyranosiduronate. This crude product was dissolved in methanol (10 ml), and 1N sodium hydroxide solution (10 ml) was added. The mixture was allowed to react at room temperature for 16 hours and concentrated under reduced pressure. The residue was extracted with ether and then subjected to Sephadex (trade mark) LH-20 column chromatography and eluted with water. The desired fraction was lyophilized to obtain the desired compound (270 mg).

EXAMPLE A-8

Sodium 1-O-[1-hydroxy-6-(12-hydroxydodeca-5,10-diyn-1-yl)-2,3,5-trimethylphenyl]-β-D-glucopyranosiduronate 1-Hydroxy-6-(12-hydroxydodeca-5,10-diyn-1-yl)-2,3,5-trimethyl-1,4-benzoquinone (326 mg, 1 mmol) was treated according to the same manner as that described in Example A-6 to obtain the desired compound (290 mg).

Elemental Analysis for $C_{27}H_{35}O_9Na \cdot 1.5H_2O$ Calcd.: C,58.58; H,6.92 Found: C,58.87; H,6.73

NMR (D$_2$O) δ (ppm): 1.561 (4H, m), 1.649 (2H, quintet, J=7.0 Hz), 2.150 (3H, s), 2.228 (3H, s), 2.283 (3H, s), 2.230 (2H), 2.280 (2H), 2.325 (2H, tt), 2.667 (2H, br.t), 3.502 (1H, d, J=9.5 Hz), 3.580 (2H, m), 3.693 (1H, dd, J=7.8,9.5 Hz), 4.162 (2H, t, J=2.1 Hz), 4.677 (1H, d, J=7.8 Hz).

IR (KBr) v: 3380, 1600 cm$^{-1}$. SIMS (H$_2$O+Glycerol): 527 (M+1), 549 (M+Na) SIMS (H$_2$O+Glycerol+0.1NKJ): 527 (M+1), 543 (M−Na+K+1), 565 (M+K), 581 (M−Na+K+K).

EXAMPLE A-9

Sodium 1-O-[4-hydroxy-6-(3-pyridylmethyl)-2,3,5-trimethylphenyl]-β-D-glucopyranosiduronate 6-(3-Pyridylmethyl)-2,3,5-trimethyl-1,4 -benzoquinone (241 mg, 1 mmol) was dissolved in dichloromethane (5 ml). The solution was stirred for 1 hour with a solution containing sodium hydrosulfite (400 mg, 2.3 mmol) in water (5 ml). The dichloromethane layer was separated, dried over anhydrous magnesium sulfate and concentrated under reduced pressure. The residue was dissolved in dichloromethane (5 ml), and tert-butylchlorodiphenylsilane (550 mg, 2 mmol) was added. Then imidazole (136 mg, 2 mmol) was added under a stream of nitrogen. The reaction mixture was stirred at 43° C. for 16 hours and washed with water (5 ml). The organic layer was dried over anhydrous magnesium sulfate and concentrated under reduced pressure to obtain crude 4-tert-butyldiphenylsilyloxy-6-(3 -pyridylmethyl)-2,3,5-trimethylphenol. This crude product was dissolved in dichloromethane (10 ml), and methyl 1-O-trichloroacetimidoyl-2,3,4-tri-O-acetyl-α-D-glucopyranosiduronate (1 g, 2.1 mmol) was added. Boron trifluoride diethyl ether (0.2 ml) was added under ice-cooling, and the mixture was stirred at the same temperature for 30 minutes. Then water (10 ml) containing sodium bicarbonate (1 g) was added, and the mixture was stirred for 5 minutes. The dichloromethane layer was separated and concentrated under reduced pressure. To the residue were added tetrahydrofuran (15 ml), methanol (10 ml) and 1N sodium hydroxide solution (20 ml), and the mixture was allowed to react at room temperature for 40 hours and concentrated under reduced pressure. The residue was extracted with ether, and the aqueous layer was subjected to Sephadex (trade mark) LH-20 column chromatography and eluted with water. The desired fraction was lyophilized to obtain the desired compound (210 mg) as white powder.

mp: 215° C. (dec.)

Elemental Analysis for $C_{21}H_{24}NO_8Na \cdot 2H_2O$ Calcd.: C,52.83; H,5.91; N,2.93 Found: C,52.76; H,5.89; N,2.88

NMR (D$_2$O) δ (ppm): 2.006 (3H, s), 2.171 (3H, s), 2.275 (3H, s), 3.400–3.682 (4H, m), 4.288 (2H, ABq, J=16,41 Hz), 4.694 (1H, d, J=8 Hz), 7.340–8.314 (4H, m).

IR (KBr) v: 3380, 1610 cm$^{-1}$. $[α]_D^{23}$=−35.5° (c=0.95, H$_2$O ).

EXAMPLE A-10

Sodium 1-O-[1-hydroxy-6-(3-pyridylmethyl)-2,3,5-trimethylphenyl]-β-D-glucopyranosiduronate 6-(3-Pyridylmethyl)-2,3,5-trimethyl-1,4 -benzoquinone (241 mg, 1 mmol) was dissolved in dichloromethane (5 ml). The solution was stirred for 1 hour with a solution containing sodium hydrosulfite (400 mg, 2.3 mmol) in water (5 ml). The dichloromethane layer was separated, dried over anhydrous magnesium sulfate and concentrated under reduced pressure. The residue was dissolved in dichloromethane (5 ml), and tert-butylchlorodiphenylsilane (550 mg, 2 mmol) was added. Then imidazole (136 mg, 2 mmol) was added under a stream of nitrogen. The reaction mixture was stirred at 43° C. for 16 hours and washed with water (5 ml). The organic layer was dried over anhydrous magnesium sulfate and concentrated under reduced pressure to obtain crude 4-tert-butyldiphenylsilyloxy-6-(3 -pyridylmethyl)-2,3,5-trimethylphenol.

This crude product was dissolved in dichloromethane (5 ml), and pyridine (0.1 ml, 1.2 mmol) followed by acetyl chloride (0.08 ml, 1.1 mmol) was added with stirring under ice-cooling. The mixture was stirred at the same temperature for 30 minutes and washed with water (5 ml). The dichloromethane layer was concentrated under reduced pressure. The residue was dissolved in tetrahydrofuran (8 ml), and tetrabutylammonium fluoride trihydrate (731 mg, 2 mmol) was added. The mixture was stirred at room temperature for 30 minutes. The reaction mixture was concentrated under reduced pressure, and the residue was dissolved in ether and washed with water. The ether layer was dried over anhydrous magnesium sulfate and concentrated under reduced pressure to obtain crude 1-acetoxy-4-hydroxy-6-(3-pyridylmethyl)-2,3,5-trimethylbenzene. This crude product was dissolved in dichloromethane (10 ml). Methyl 1-O-trichloroacetimidoyl-2,3,4-tri-O-acetyl-α-D-glucopyranuronate (1.4 g, 3 mmol) was added, and boron trifluoride diethyl ether (0.2 ml) was added under ice-cooling. The mixture was stirred at the same temperature for 30 minutes. Then water (10 ml) containing sodium bicarbonate (1 g) was added, and the mixture was stirred for 5 minutes. The dichloromethane layer was separated and concentrated under reduced pressure to obtain crude methyl 1-O-[1-acetoxy-6-(3-pyridylmethyl)-2,3,5-trimethylphenyl]-2,3,4-tri-O-acetyl-β-D-glucopyranosiduronate. This crude product was dissolved in methanol (10 ml), and 1N sodium hydroxide solution (10 ml) was added. The mixture was allowed to react at room temperature for 16 hours and concentrated under reduced pressure. The residue was extracted with ether, and the aqueous layer was subjected to Sephadex (trade mark) LH-20 column chromatography and eluted with water. The desired fraction was lyophilized to obtain the desired compound (200 mg).

mp: 210° C. (dec.)

Elemental Analysis for $C_{21}H_{24}NO_8Na \cdot 1.5H_2O$ Calcd.: C,53.85; H,5.81; N,2.99 Found: C,54.12; H,6.07:N,2.95

NMR ($D_2O$) δ (ppm): 2.155 (3H, s), 2.208 (3H, s ), 2.261 (3H, s), 3.473–3.750 (4H, m), 4.073 (2H, s), 4.679 (1H, d, J=8 Hz), 7.290–8.326 (4H, m).

IR (KBr) v: 3410, 1610, 1055 $cm^{-1}$.

REFERENCE EXAMPLE 3

Disodium
1-O-[6-(11-carboxyundeca-5,10-diyn-1-yl)-4-hydroxy-2,3,5-trimethylphenyl]-β-D-glucopyranosiduronate 6-(11-Carboxyundeca-5,10-diyn-1-yl)-2,3,5-trimethyl-1,4-benzoquinone (340 mg, 1 mmol) was dissolved in ether (10 ml). A solution of diazomethane in ether was added under ice-cooling for methyl-esterification. Nitrogen gas was introduced to remove excess diazomethane. Then water (5 ml) containing sodium hydrosulfite (400 mg, 2.3 mmol) was added, and the mixture was stirred for 1 hour. The ether layer was separated, dried over anhydrous magnesium sulfate and concentrated under reduced pressure. The residue was dissolved in dichloromethane (5 ml), and tert-butylchlorodiphenylsilane (550 mg, 2 mmol) was added. Then imidazole (136 mg, 2 mmol) was added under a stream of nitrogen, and the mixture was stirred at 43° C. for 16 hours. The reaction mixture was washed with water (5 ml), and the organic layer was dried over anhydrous magnesium sulfate and concentrated under reduced pressure to obtain crude 4-tert-butyldiphenylsilyloxy-6-(11-methoxycarbonylundeca-5,10-diyn-1-yl)-2,3,5-trimethylphenol. This crude product was dissolved in dichloromethane (10 ml), and methyl 1-O-trichloroacetimidoyl-2,3,4-tri-O-acetyl-α-D-glucopyranosiduronate (1 g, 2.1 mmol) was added. Boron trifluoride diethyl ether (0.2 ml) was added under reduced pressure, and the mixture was stirred at the same temperature for 30 minutes. Then water (10 ml) containing sodium bicarbonate (1 g) was added, and the mixture was stirred for 5 minutes. The dichloromethane layer was separated and concentrated under reduced pressure. To the residue were added tetrahydrofuran (15 ml), methanol (10 ml) and 1N sodium hydroxide solution (20 ml), and the mixture was allowed to react at room temperature for 40 hours and concentrated under reduced pressure. The residue was extracted with ether and the aqueous layer was subjected to Sephadex (trade mark) LH-20 column chromatography and eluted with water. The desired fraction was lyophilized to obtain the desired compound (290 mg) as white powder.

Elemental Analysis for $C_{27}H_{32}O_{10}Na_2 \cdot 2.5H_2O$ Calcd.: C,53.38; H,6.14 Found: C,53.40; H,6.34

NMR ($D_2O$) δ (ppm): 1.54 (4H, m), 1.69 (2H, quintet), 2.15 (3H, s), 2.21 (3H, s), 2.23 (3H, s), 2.25–2.30 (4H, m), 2.38 (2H, t), 2.74–2.84 (2H, m), 3.49 (1H, d), 3.59 (2H, m), 3.68 (1H, t), 4.69 (1H, d, J=7.6 Hz).

IR (KBr) v: 3400, 2230, 1580 $cm^{-1}$. SIMS ($H_2O$ +Glycerol): 563 (M+1), 585 (M+Na). SIMS ($H_2O$ +Glycerol+ 0.1NKJ): 563 (M+1), 579 (M–Na+K+1), 585 (M+Na), 601 (M+K).

REFERENCE EXAMPLE 4

Disodium
1-O-[6-(11-carboxyundeca-5,10-diyn-1-yl)-1-hydroxy-2,3,5-trimethylphenyl]-β-D-glucopyranosiduronate 6-(11-Carboxyundeca-5,10-diyn-1-yl)-2,3,5-trimethyl-1,4-benzoquinone (340 mg, 1 mmol) was dissolved in ether (10 ml). A solution of diazomethane in ether was added under ice-cooling for methyl-esterification. Nitrogen gas was introduced to remove excess diazomethane. Then water (5 ml) containing sodium hydrosulfite (400 mg, 2.3 mmol) was added, and the mixture was stirred for 1 hour. The ether layer was separated, dried over anhydrous magnesium sulfate and concentrated under reduced pressure. The residue was dissolved in dichloromethane (5 ml), and tert-butylchlorodiphenylsilane (550 mg, 2 mmol) was added. Then imidazole (136 mg, 2 mmol) was added under a stream of nitrogen, and the mixture was stirred at 43° C. for 16 hours. The reaction mixture was washed with water (5 ml), and the organic layer was dried over anhydrous magnesium sulfate and concentrated under reduced pressure to obtain crude 4-tert-butyldiphenylsilyloxy-6-(11 -methoxycarbonylundeca-5,10-diyn-1-yl)-2,3,5-trimethylphenol. This crude product was dissolved in dichloromethane (5 ml), and pyridine (0.1 ml, 1.2 mmol) followed by acetyl chloride. (0.08 ml, 1.1 mmol) was added with stirring under ice-cooling. The mixture was stirred at the same temperature for 30 minutes and washed with water (5 ml). The dichloromethane layer was concentrated under reduced pressure. The residue was dissolved in tetrahydrofuran (8 ml), and tetrabutylammonium fluoride trihydrate (731 mg, 2 mmol) was added. The mixture was stirred at room temperature for 30 minutes. The reaction mixture was concentrated under reduced pressure, and the residue was dissolved in ether and washed with water. The ether layer was dried over anhydrous magnesium sulfate and concentrated under reduced pressure to obtain crude 1-acetoxy-4-hydroxy-6-(11-methoxycarbonylundeca-5,10-diyn-1-yl)-2,3,5-trimethylbenzene. This crude product was dissolved in dichloromethane (10 ml). Methyl 1-O-trichloroacetimidoyl-2,3,4-tri-O-acetyl-α-D-glucopyranosiduronate (1.4 g, 3 mmol) was added, and boron trifluoride diethyl ether (0.2 ml) was added under ice-cooling. The mixture was stirred at the same temperature for 30 minutes. Then water (10 ml) containing sodium bicarbonate (1 g) was added, and the mixture was stirred for 5 minutes. The dichloromethane layer was separated and concentrated under reduced pressure to obtain crude methyl 1-O-[1-acetoxy-6-(11-methoxycarbonylundeca-5,10-diyn-1-yl)-2,3,5-trimethylphenyl]-2,3,4-tri-O-acetyl-β-D-glucopyranosiduronate. This crude product was dissolved in methanol (10 ml), and 1N sodium hydroxide solution (10 ml) was added. The mixture was allowed to react at room temperature for 16 hours and concentrated under reduced pressure. The residue was extracted with ether, and the aqueous layer was subjected to Sephadex (trade mark) LH-20 column chromatography and eluted with water. The desired fraction was lyophilized to obtain the desired compound (265 mg).

Elemental Analysis for $C_{27}H_{32}O_{10}Na_2 \cdot 2.5H_2O$ Calcd.: C,53.38; H,6.14 Found: C,53.65; H,5.84

NMR ($D_2O$) δ (ppm): 1.56 (4H, m), 1.69 (2H, quintet), 2.15 (3H, s), 2.23 (3H, s), 2.28 (3H, s), 2.20– 2.30 (4H, m), 2.38 (2H, t), 2.67 (2H, br.t), 3.50 (1H, d), 3.59 (2H, m), 3.69 (1H, t), 4.68 (1H, d, J=7.8 Hz).

IR (KBr): ν 3400, 2220, 1580 $cm^{-1}$. SIMS ($H_2O$ +Glycerol): 563 (M+1), 585 (M+Na). SIMS ($H_2O$ +Glycerol+ 0.1NKJ): 563 (M+1), 579 (M−Na+K+1), 585 (M+Na), 601 (M+K).

REFERENCE EXAMPLE 5

Sodium 2,3-dimethoxy-1-hydroxy-6-(10-hydroxydecyl)-5-methylphenyl-4-sulfate

1-Acetoxy-6-(10-acetoxydecyl)-2,3-dimethoxy-4-hydroxy-5-methylbenzene (2.1 g) obtained in Example A-5 was dissolved in dimethylformamide (10 ml). Sulfur trioxide-pyridine complex (1.6 g) was added, and the mixture was allowed to react at room temperature for 5 hours followed by removal of dimethylformamide under reduced pressure. The residue was dissolved in methanol (20 ml), and 1N sodium hydroxide solution (25 ml) was added. The mixture was heated at 50 °C. for 10 minutes. After concentration under reduced pressure, the residue was subjected to Amberlite (trade mark) XAD-II column chromatography and eluted with water followed by 50% ethanol/water. The desired fraction was concentrated and lyophilized. The desired compound thus obtained was dissolved in a small amount of methanol, and 10 fold amount of ethyl acetate was added for crystallization to obtain crystals (1.4 g).

mp: 146°–147° C. (dec.)

Elemental Analysis for $C_{19}H_{31}O_8SNa$ Calcd.: C,51.57; H,7.06 Found : C,51.26; H,7.03

NMR ($D_2O$) δ (ppm): 1.21 (16H, br.s), 2.21 (3H, s), 2.55 (2H, t, J=7.90 Hz), 3.54 (2H, t, J=6.60 Hz), 3.81 (3H, s), 3.88 (3H, s).

IR (KBr) ν: 1615, 1585, 1485, 1465, 1425, 1365, 1275, 1255, 1120, 1100, 1060, 1005, 950, 940, 790, 755, 725, 675, 630, 610 $cm^{-1}$.

REFERENCE EXAMPLE 6

Sodium 2,3-dimethoxy-4-hydroxy-6-(10-hydroxydecyl)-5-methylphenyl-1-sulfate 6-(10-Acetoxydecyl)-4-tert-butyldiphenylsilyloxy-2,3-dimethoxy-5-methylphenol (3.10 g) obtained in Example B-1 was dissolved in dimethylformamide (15 ml). Sulfur trioxide-pyridine complex (1.6 g) was added, and the mixture was stirred at room temperature for 5 hours. The reaction mixture was concentrated under reduced pressure. The residue was dissolved in methanol (20 ml), 1N sodium hydroxide solution (25 ml) was added, and the mixture was stirred at room temperature for 3 days. The solvent was distilled off under reduced pressure, and the residue was extracted with ether. The aqueous layer was subjected to Amberlite (trade mark) XAD-II column chromatography and eluted with water followed by 50% ethanol/water. The desired fraction was concentrated and then lyophilized. The desired compound thus obtained was crystallized from methanol/ethyl acetate to obtain crystals (1.3 g).

mp: 136°–137° C.

Elemental Analysis for $C_{19}H_{31}O_8SNa \cdot 0.5H_2O$ Calcd.: C,50.54; H,7.14 Found: C,50.79; H,7.10

NMR ($D_2O$) δ (ppm): 1.10–1.60 (16H, m), 2.11 (3H, s), 2.70 (2H, t, J=7.9 Hz), 3.55 (2H, t, J=6.6 Hz), 3.82 (3H, s), 3.89 (3H, s).

IR (KBr) ν: 3400, 2925, 2850, 1480, 1460, 1425, 1380, 1365, 1255, 1220, 1115, 1095, 1040, 1000, 960, 930, 790, 770, 590 $cm^{-1}$.

REFERENCE EXAMPLE 7

Sodium 2,3-dimethoxy-4-hydroxy-6-(10-hydroxydecyl)-5-methylphenyl-1-sulfate 2,3-Dimethoxy-6-(10-hydroxydecyl)-5-methylbenzoquinone (3.38 g, 10 mmol) was dissolved in dichloromethane (50 ml). Pyridine (1 ml) followed by acetyl chloride (0.8 ml) was added with stirring under ice-cooling, and the mixture was stirred for 1 hour. Water (5 ml) was added to the reaction mixture which was then stirred for 20 minutes. Then sodium hydrosulfite (4 g) was added, and the mixture was stirred at room temperature for 2 hours. The dichloromethane layer was separated, dried over anhydrous magnesium sulfate and concentrated under reduced pressure. The residue was dissolved in dichloromethane (50 ml), and tert-butylchlorodiphenylsilane (5.5 g, 20 mmol) and imidazole (1.36 g, 20 mmol) were added. The mixture was stirred at 43° C. for 16 hours under a stream of nitrogen. The reaction mixture was washed with water, dried over anhydrous magnesium sulfate and concentrated under reduced pressure to obtain crude 6-(10-acetoxydecyl)-4-tert-butyldiphenylsilyloxy-2,3-dimethoxy-5-methylphenol. The concentrate was dissolved in dimethylformamide (15 ml). Sulfur trioxide-pyridine complex (3.2 g, 20 mmol) was added, and the mixture was stirred at room temperature for 5 hours. The reaction mixture was concentrated under reduced pressure. The residue was dissolved in methanol (40 ml), and 1N sodium hydroxide solution (60 ml) was added. The mixture was allowed to react for 16 hours. Methanol was distilled off under reduced pressure, and the residue was extracted with ether. The aqueous layer was subjected to Amberlite (trade mark) XAD-II column chromatography and eluted with water followed by 50% ethanol/water. The desired fraction was concentrated and lyophilized to obtain the desired compound (2.8 g).

REFERENCE EXAMPLE 8

Sodium 2,3-dimethoxy-1-hydroxy-6-(10-hydroxydecyl)-5-methylphenyl-4-sulfate 2,3-Dimethoxy-6-(10-hydroxydecyl)-5-methylbenzoquinone (3.38 mg, 10 mmol) was dissolved in dichloromethane (50 ml). Pyridine (1 ml) followed by acetyl chloride (0.8 ml) was added with stirring under ice-cooling. The mixture was stirred for 1 hour. Water (50 ml) was added to the reaction mixture which was then stirred for 20 minutes. Then sodium hydrosulfite (4 g) was added, and the mixture was stirred at room temperature for 2 hours. The dichloromethane layer was separated, dried over anhydrous magnesium sulfate and concentrated under reduced pressure. The residue was dissolved in dichloromethane (50 ml), and tert-butylchlorodiphenylsilane (5.5 g, 20 mmol) and imidazole (1.36 g, 20 mmol) were added. The mixture was stirred at 43° C. for 16 hours under a stream of nitrogen. The reaction mixture was washed with water, dried over anhydrous magnesium sulfate and concentrated under reduced pressure to obtain crude 6-(10-acetoxydecyl)-4-tert-butyl diphenylsilyloxy-2,3-dimethoxy-5-methylphenol. The concentrate was dissolved in dichloromethane (100 ml). Triethylamine (2 ml) followed by acetyl chloride (0.8 ml) was added, and the mixture was stirred for 30 minutes. The reaction mixture was washed with water and concentrated under reduced pressure. The residue was dissolved in tetrahydrofuran (50 ml), and tetrabutylammonium fluoride trihydrate (1.3 g, 50 mmol) was added. The mixture was stirred at room temperature for 30 minutes. The reaction mixture was concentrated under reduced pressure, and the residue was dissolved in dichloromethane, washed with water and then dried over anhydrous magnesium sulfate. The dichloromethane layer was concentrated under reduced pressure to obtain crude 1-acetoxy-6-(10-acetoxydecyl)-2,3-dimethoxy-4-hydroxy-5-methylbenzene. This crude product was dissolved in dimethylformamide (15 ml). Sulfur trioxide-pyridine complex (6.4 g, 40 mmol) was added, and the mixture was allowed to react for 5 hours at room temperature. The reaction mixture was concentrated under reduced pressure. The residue was-dissolved in methanol (40 ml), 1N sodium hydroxide solution (30 ml) was added, and the mixture was stirred at room temperature for 16 hours. The reaction mixture was concentrated under reduced pressure, and the residue was extracted with ether. The aqueous layer was subjected to Amberlite (trade mark) XAD-II column chromatography and eluted with water followed by 50% ethanol/water. The desired fraction was lyophilized to obtain the desired compound (2.4 g).

EXAMPLE A-11

Sodium 4-hydroxy-6-(3-pyridylmethyl)-2,3,5-trimethylphenyl-1-sulfate 6-(3-Pyridylmethyl)-2,3,5-trimethyl-1,4 -benzoquinone (2.41 g, 10 mmol) was dissolved in dichloromethane (50 ml). The solution was stirred with water (50 ml) containing sodium hydrosulfite (4 g) for 2 hours. According to the same manner as that described in Reference Example 7, the mixture was subjected to tert-butyldiphenylsilylation, sulfonation and hydrolysis to obtain the desired compound (2.11 g).

mp: 210°–215° C. (dec.)

Elemental Analysis for $C_{15}H_{16}NO_5SNa \cdot 0.9H_2O$ Calcd.: C,49.83; H,4.96; N,3.87 Found: C,50.03; H,5.01; N,3.91

NMR ($D_2$) δ (ppm): 2.164 (3H, s), 2.195 (3H, s), 2.259 (3H, s), 4.079 (2H, s), 7.318–8.326 (4H, m).

IR (KBr) v: 3450, 1630, 1245, 1040 cm$^{-1}$.

REFERENCE EXAMPLE 9

Sodium 4-hydroxy-6-(12-hydroxydodeca-5,10-diyn-1-yl)-2,3,5-trimethylphenyl-1-sulfate 6-(12-Hydroxydodeca-5,10-diyn-1-yl)-2,3,5 -trimethyl-1,4-benzoquinone (3.26 g, 10 mmol) was treated according to the same manner as that described in Reference Example 7 to obtain the desired compound (3.05 g).

Elemental Analysis for $C_{21}H_{27}O_6SNa \cdot 1.5H_2O$ Calcd.: C,55.13; H,6.61 Found: C,55.33; H,6.37

NMR (CDCl$_3$+CD$_3$OD) δ (ppm): 1.35–1.83 (6H, s), 2.12 (3H, s), 2.17 (3H, s), 2.26 (3H, s), 2.00–2.43 (6H, m), 2.86 (2H, m), 4.16 (2H, t, J=2 Hz).

IR (KBr) v: 3440, 1240, 1035 cm$^{-1}$.

EXAMPLE A-12

Sodium 1-hydroxy-6-(3-pyridylmethyl)-2,3,5-trimethylphenyl-4-sulfate 6-(3-Pyridylmethyl)-2,3,5-trimethyl-1,4 -benzoquinone (2.41 g, 10 mmol) was dissolved in dichloromethane (50 ml). The solution was stirred with water (50 ml) containing sodium hydrosulfite (4 g) for 2 hours. The hydroquinone thus obtained was treated according to the same manner as that described in Reference Example 8 to obtain the desired compound (1.95 g).

mp: 182°–193° C.

Elemental Analysis for $C_{15}H_{16}NO_5SNa \cdot 1.2H_2O$ Calcd.: C,49.10; H,5.05; N,3.82 Found: C,49.12; H,5.12; N,3.84

NMR (D$_2$O) δ : 2.054 (3H, s), 2.180 (3H, s), 2.257 (3H, s), 4.254 (2H, s), 7.288–8.300 (4H, m).

IR (KBr) v: 3440, 1635, 1245, 1030 cm$^{-1}$.

REFERENCE EXAMPLE 10

Sodium 1-hydroxy-6-(12-hydroxydodeca-5,10-diyn-1-yl)-2,3,5-trimethylphenyl-4-sulfate 6-(12-Hydroxydodeca-5,10-diyn-1-yl)-2,3,5 -trimethyl-1,4-benzoquinone (3.26 g, 10 mmol) was treated according to the same manner as that described in Reference Example 8 to obtain the desired compound (2.88 g).

Elemental Analysis for $C_{21}H_{27}O_6SNa \cdot 1.5H_2O$ Calcd.: C,55.13; H,6.61 Found: C,54.88; H,6.35

NMR (CDCl$_3$+CD$_3$OD) δ (ppm): 1.35–1.83 (6H, m), 2.12 (3H, s), 2.26 (3H, s), 2.31 (3H, s), 2.00–2.43 (6H, m), 2.62 (2H, m), 4.16 (2H, t, J=2 Hz).

IR (KBr) v: 3460, 1235, 1040 cm$^{-1}$.

EXAMPLE A-13

Sodium 2,3-dimethoxy-4-hydroxy-6-(10-hydroxydecyl)-5-methylphenyl-1-phosphate 6-(10-Acetoxydecyl)-4-tert-butyldiphenylsilyloxy-2,3-dimethoxy-5-methylphenol (6 g, 10 mmol) obtained in Example B-1 was dissolved in toluene (50 ml), and phosphorus oxychloride (4.8 ml) was added. Pyridine (1.6 ml) was added with stirring under ice-cooling, and then the mixture was stirred at room temperature for 2 hours. The mixture was concentrated under reduced pressure, and ice water (50 ml) and ethyl acetate (50 ml) were added to the residue. The organic layer was separated and concentrated under reduced pressure. The residue was dissolved by adding tetrahydrofuran (30 ml) and methanol (70 ml) thereto. 1N Sodium hydroxide solution (100 ml) was added under ice-cooling, and then the mixture was stirred at room temperature overnight. The solvent was distilled off under reduced pressure, acetic acid (6 ml) was added, and the mixture was extracted with hexane. The aqueous layer was subjected to Amberlite (trade mark) XAD-II column chromatography and eluted with water followed by 50% methanol/water. The desired fraction was concentrated and lyophilized, and ethanol (2 ml) was added to the powder thus obtained for crystallization. The crystals were separated by filtration, washed with ethyl acetate followed by hexane to obtain the desired compound (1.58 g).

mp: 163.7°–165° C.

Elemental Analysis for $C_{19}H_{32}O_8PNa$ Calcd.: C,51.58; H,7.29; P,7.00 Found: C,51.33; H.7.46; P,6.75

NMR ($D_2O$) δ (ppm): 1.20–1.60 (16H, m), 2.17 (3H, s), 2.67 (2H, m), 3.61 (2H, t, J=6.6 Hz), 3.88 (3H, s), 3.91 (3H, s).

IR (KBr) ν: 3540, 2925, 2850, 1480, 1470, 1455, 1435, 1380, 1370, 1205, 1125, 1100, 1055, 945, 930, 805, 535 $cm^{-1}$.

EXAMPLE A-14

Sodium 2,3-dimethoxy-1-hydroxy-6-(10-hydroxydecyl)-5-methylphenyl-4-phosphate

1-Acetoxy-6-(10-acetoxydecyl)-2,3-dimethoxy-4-hydroxy-5-methylbenzene (4.2 g, 10 mmol) obtained in Example A-5 was dissolved in toluene (15 ml), and phosphorus oxychloride (1.9 ml, 20 mmol) was added, Pyridine (1.6 ml, 20 mmol) was added with stirring under ice-cooling, and then the mixture was stirred at room temperature for 2 hours. The reaction mixture was concentrated under reduced pressure, and ice water (50 ml) and ethyl acetate (50 ml) were added to the residue. The organic layer was separated and concentrated under reduced pressure. Then the residue was dissolved in tetrahydrofuran (50 ml). 1N Sodium hydroxide solution (100 ml) was added under ice-cooling, and then the mixture was stirred at room temperature for 45 minutes. The mixture was concentrated under reduced pressure, acetic acid (6 ml) was added to the residue, and the mixture was extracted with hexane. The aqueous layer was subjected to Amberlite (trade mark) XAD-II column chromatography and eluted with water followed by 50% methanol/water. The desired fraction was concentrated and lyophilized. The white powder thus obtained was dissolved in methanol and concentrated for crystallization. The crystals were separated by filtration, washed with ethyl acetate followed by hexane to obtain the desired compound (2.0 g).

mp: 158°–160° C.

Elemental Analysis for $C_{19}H_{32}O_8PNa$ Calcd.: C,51.58; H,7.29; P,7.00 Found: C,51.56; H.7.38; P,7.01

NMR ($D_2O$) δ (ppm): 1.20–1.60 (16H, m), 2.24 (3H, s), 2.61 (2H, m), 3.59 (2H, t, J=6.6 Hz), 3.87 (3H, s), 3.91 (3H, s).

IR (KBr) ν: 3525, 3400, 2925, 2850, 1480, 1460, 1430, 1370, 1190, 1120, 1060, 940, 805, 520 $cm^{-1}$.

EXAMPLE A-15

1-O-[2,3-Dimethoxy-4-hydroxy-6-(10-hydroxydecyl)-5-methylphenyl]-β-D-glucopyranoside 6-(10-Acetoxydecyl)-4-tert-butyldiphenylsilyloxy-2,3-dimethoxy-5-methylphenol (6.2 g) obtained in Example B-1 was dissolved in dichloromethane (40 ml). O-(2,3,4,6-Tetra-O-acetyl-α-D-glucopyranosyl)trichloroacetimidate (R. R. Schmidt et al., Angew. Chem. Int. Ed. Engl., 19, 731 (1980)) (6 g) was added, and the mixture was ice-cooled. Boron trifluoride diethyl ether (2 ml) was added with stirring, and the mixture was allowed to react at the same temperature for 30 minutes. Then water (50 ml) containing sodium bicarbonate (2 g) was added. The organic layer was separated and concentrated under reduced pressure. The residue was dissolved in tetrahydrofuran (50 ml), and tetrabutylammonium fluoride trihydrate (2 g) was added. The mixture was stirred for 30 minutes. After concentration under reduced pressure, the residue was subjected to column chromatography on silica gel and eluted with hexane/ethyl acetate (7:3). The eluate was concentrated under reduced pressure. The residue was dissolved by adding methanol (30 ml) and tetrahydrofuran (15 ml) thereto. 1N Sodium hydroxide solution (40 ml) was added, and the mixture was stirred at room temperature overnight. After concentrating the reaction mixture under reduced pressure, ethyl acetate (200 ml) was added and 1N hydrochloric acid solution (40 ml) was added under ice-cooling. The ethyl acetate layer was dried over anhydrous magnesium sulfate, and the solvent was distilled off. The crystals thus obtained were separated by filtration and recrystallized from methanol/ether to obtain the desired compound (1.2 g).

mp: 163°–165° C.

Elemental Analysis for $C_{25}H_{42}O_{10} \cdot 0.2H_2O$ Calcd.: C,59.32; H,8.44 Found: C,59.34; H,8.63

NMR (DMSO-$d_6$) δ (ppm): 1.26 (16H, m), 2.03 (3H, s), 2.60 (2H, m), 3.72 (3H, s), 3.77 (3H, s), 4.27 (2H, m), 4.71 (1H, d, J=7.4 Hz), 4.91 (1H, d, J=4.6 Hz), 5.00 (1H, d, J=4.0 Hz), 5.14 (1H, d, J=4.2 Hz), 8.32 (1H, s).

IR (KBr) ν: 2930, 2860, 1470, 1435, 1395, 1390, 1370, 1110, 1065, 1040, 1020, 1000, 970, 925, 895, 650, 620 $cm^{-1}$. $[\alpha]_D^{25} = -18.7°$ (c=1.215, MeOH)

EXAMPLE A-16

1-O-[2,3-Dimethoxy-1-hydroxy-6-(10-hydroxydecyl)-5-methylphenyl]-β-D-glucopyranoside 1-Acetoxy-6-(10-acetoxydecyl)-2,3-dimethoxy-4-hydroxy-5-methylbenzene (2.1 g) obtained in Example A-5 was dissolved in dichloromethane (20 ml). O-(2,3,4,6-Tetra-O-acetyl-α-D-glucopyranosyl)trichloroacetimidate (3 g) was added, and the mixture was ice-cooled. Boron trifluoride diethyl ether (1 ml) was added with stirring, and the mixture was allowed to react at the same temperature for 30 minutes. Then water (20 ml) containing sodium bicarbonate (0.5 g) was added. The organic layer was concentrated under reduced pressure. The residue was dissolved in methanol (10 ml), 1N sodium hydroxide solution (10 ml) was added, and the mixture was stirred at room temperature overnight. After concentration under reduced pressure, 1N hydrochloric acid solution (10 ml) was added under ice-cooling, and the mixture was extracted with ethyl acetate. The organic layer was dried over anhydrous magnesium sulfate and concentrated under reduced pressure to obtain the desired compound as crystals (1.2 g).

mp: 130°–131° C.

Elemental Analysis for $C_{25}H_{42}O_{10}$ Calcd.: C,59.74; H,8.42 Found: C,59.42; H,8.53

NMR ($CDCl_3$-DMSO-$d_6$) δ (ppm): 1.29 (16H, br.s), 2.23 (3H, s), 3.88 (3H, s), 3.90 (3H, s), 4.42 (2H, m), 4.61 (1H, d, J=7.0 Hz), 6.58 (1H, s).

IR (KBr) ν: 2930, 2860, 1470, 1430, 1370, 1310, 1100, 1070, 1000 $cm^{-1}$. $[\alpha]_D^{25} = -16.2°$ (c=0.993, MeOH)

EXAMPLE A-17

2,3-Dimethoxy-4-hydroxy-6-(10-hydroxydecyl)-5-methyl-1-(4-pyridylmethyloxy)benzene hydrochloride A mixture of 6-(10-acetoxydecyl)-4-tert-butyldiphenylsilyloxy- 2,3-dimethoxy-5-methylphenol (3.70 g) obtained in Example B-1, 4-chloromethylpyridine hydrochloride (1.96 g), potassium carbonate (5.00 g) and dimethylformamide (30 ml) was stirred at room temperature for 16 hours. Water was added to the reaction mixture, and the mixture was extracted with ethyl acetate. The organic layer was concentrated under reduced pressure, and the residue was dissolved in tetrahydrofuran (30 ml). Tetrabutylammonium fluoride trihydrate (1 g) was added, and the mixture was stirred at room temperature for 1 hour. The mixture was concentrated under reduced pressure. Methanol (50 ml) and 1N sodium hydroxide solution (10 ml) were added to the residue, and the mixture was stirred at room temperature for 16 hours. After concentration, the residue was subjected to column chromatography on silica gel and eluted with ethyl acetate. The desired fraction was concentrated. The residue was dissolved in ethanol (30 ml), and conc. hydrochloric acid (0.7 ml) was added. The crystals obtained after concentration under reduced pressure were separated by filtration and washed with ether to obtain the desired compound (1.2 g).

mp: 145°–147° C.

Elemental Analysis for $C_{25}H_{37}NO_5 \cdot HCl \cdot 0.1H_2O$ Calcd.: C,63.91; H,8.20; N,2.98 Found: C,63.85; H,8.39; N,2.96

NMR (DMSO-$d_6$) δ (ppm): (16H, s), 2.06 (3H, s), 3.36 (2H, t, J=6.6 Hz), 3.73 (3H, s), 3.77 (3H, s), 5.19 (2H, s), 8.06 (2H, d, J=6.0 Hz), 8.93 (2H, d, J=6.0 Hz).

IR (KBr) ν: 3325, 2925, 2850, 1640, 1600, 1510, 1470, 1430, 1380, 1360, 1120, 1100, 1050, 970, 800 cm$^{-1}$.

EXAMPLE A-18

2,3-Dimethoxy-6-(10-hydroxydecyl)-4-(2-pyridylmethyloxy)-5-methylphenol hydrochloride A mixture of 1-acetoxy-6-(10-acetoxydecyl)-2,3-dimethoxy-4-hydroxy-5-methylbenzene (2.1 g) obtained in Example A-5, 2-chloromethylpyridine hydrochloride (2 g), potassium carbonate (5 g) and dimethylformamide (15 ml) was stirred at room temperature for 16 hours. The reaction mixture was poured into water, and the mixture was extracted with ethyl acetate. The organic layer was concentrated under reduced pressure, and the residue was dissolved in methanol (20 ml). Aqueous 1N sodium hydroxide solution (20 ml) was added, and the mixture was stirred at room temperature overnight. The reaction mixture was concentrated under reduced pressure. The residue was subjected to column chromatography on silica gel and eluted with ethyl acetate, and the eluate was concentrated. The residue was dissolved by adding ethanol (30 ml), and conc. hydrochloric acid (0.7 ml) was added. The crystals obtained after concentration under reduced pressure were separated by filtration using ether to obtain the desired compound (1.7 g).

mp: 127°–130° C.

Elemental Analysis for $C_{25}H_{37}NO_5 \cdot HCl \cdot 0.1H_2O$ Calcd.: C,63.91; H,8.20; N,2.98 Found: C,63.84; H,8.27; N,2.96

NMR (DMSO-$d_6$) δ (ppm): 1.26 (16H, s), 2.08 (3H, s), 3.37 (2H, t, J=6.6 Hz), 3.72 (3H, s), 3.76 (3H, s), 5.11 (2H, s), 7.70–8.80 (4H, m).

IR (KBr) ν: 2925, 2850, 1635, 1620, 1540, 1475, 1460, 1420, 1360, 1120, 1100, 1060, 1005, 965, 770 cm$^{-1}$.

REFERENCE EXAMPLE 11

2,3-Dimethoxy-5-methyl-6-(10-trityloxydecyl)-hydroquinone 2,3-Dimethoxy-6-(10-hydroxydecyl)-5-methylbenzoquinone (33.8 g) was dissolved in dichloromethane (250 ml). Trityl chloride (30 g) followed by triethylamine (10 g) was added, and the mixture was stirred at room temperature overnight. Then water (250 ml) containing sodium hydrosulfite (40 g) was added, and the mixture was stirred at room temperature for 1 hour. The organic layer was separated, dried over anhydrous magnesium sulfate and concentrated under reduced pressure to obtain the desired compound (80.4 g).

NMR (CDCl$_3$) δ (ppm): 1.25 (16H, br.s), 2.15 (3H, s), 2.60 (2H, t, J=7.9 Hz), 3.88 (6H, s), 5.25–5.32 (4H, m), 7.21–7.46 (15H, m).

EXAMPLE B-3

4-tert-Butyldiphenylsilyloxy-2,3-dimethoxy-5-methyl-6-(10-trityloxydecyl)phenol 2,3-Dimethoxy-5-methyl-6-(10-trityloxydecyl)hydroquinone (80.4 g) was dissolved in dichloromethane (250 ml). tert-Butylchlorodiphenylsilane (26 ml) and imidazole (6.8 g) were added, and the mixture was stirred at 40° C. for 21 hours. The reaction mixture was washed with water, dried over anhydrous magnesium sulfate and concentrated. The residue was subjected to column chromatography on silica gel and eluted with hexane/ethyl acetate (9:1) to obtain the desired compound (40 g).

NMR (CDCl$_3$) δ (ppm): 1.26 (16H, br.s), 2.26 (3H, s), 2.59 (2H, t, J=7.9 Hz), 2.90 (3H, s), 3.88 (3H, s), 3.04 (2H, t, J=6.6 Hz), 5.29 (1H, s), 7.15–7.80 (15H, m).

IR (KBr) ν: 3500, 2925, 2850, 1740, 1590, 1460, 1425, 1380, 1265, 1190, 1100, 1060, 970, 825, 745, 700 cm$^{-1}$.

EXAMPLE B-4

1-tert-Butoxycarbonyloxy-2,3-dimethoxy-4-hydroxy-5-methyl-6-(10-trityloxydecyl)benzene A mixture of 4-tert-butyldiphenylsilyloxy-2,3-dimethoxy-5-methyl-6-(10-trityloxydecyl)phenol (8 g), di-tert-butyl dicarbonate (3 g), triethylamine (1 g) and dichloromethane (20 ml) was stirred at 40° C. for 16 hours. After concentration under reduced pressure, the residue was dissolved in tetrahydrofuran (30 ml). Tetrabutylammonium fluoride trihydrate (2 g) was added, and the mixture was stirred at room temperature for 15 minutes. The solvent was distilled off under reduced pressure, and the residue was subjected to column chromatography on silica gel and eluted with hexane/ethyl acetate (7:3) to obtain the desired compound (10 g).

NMR (CDCl$_3$) δ (ppm): 1.15–1.70 (16H, s), 1.55 (9H, s), 2.15 (3H, s), 2.48 (2H, t, J=7.9 Hz), 3.03 (2H, t, J=6.6 Hz), 3.58 (3H, s), 3.90 (3H, s), 5.70 (1H, s), 7.15–7.75 (15H, m).

EXAMPLE A-19

2,3-Dimethoxy-6-(10-hydroxydecyl)-5-methyl-4-nicotinoyloxyphenol hydrochloride

Nicotinoyl chloride hydrochloride (2 g) was added under ice-cooling to a mixture of 1-tert-butoxycarbonyloxy-2,3-dimethoxy-4-hydroxy-6-(10-trityloxydecyl)-5 -methylbenzene (10 g), triethylamine (2 g) and dichloromethane (30 ml), and the resulting mixture was stirred at room temperature for 1 hour. The reaction mixture was washed with water followed by an aqueous solution of sodium bicarbonate, dried over anhydrous magnesium sulfate and concentrated under reduced pressure. The residue was subjected to column chromatography on silica gel and eluted with ethyl acetate/hexane (1:1) to obtain 1 -tert-butoxycarbonyloxy-2,3-dimethoxy-6-(10-trityloxydecyl)-5-methyl-4 -nicotinoyloxybenzene (5.1 g). This compound was dissolved in methanol (35 ml). Concentrated hydrochloric acid (2 ml) was added, and the mixture was heated under reflux for 30 minutes. The mixture was concentrated under reduced pressure. Ether was added to the residue which was then separated by filtration to obtain the desired compound (2.9 g).

mp: 135°–140° C. (HCl salt), mp: 84°–85° C. (free compound).

Elemental Analysis for $C_{25}H_{35}NO_6 \cdot HCl$ Calcd.: C,62.30; H,7.53; N,2.91 Found: C,62.08; H,7.54; N,2.90

NMR (DMSO-$d_6$) δ (ppm): 1.26 (16H, br.s), 2.01 (3H, s), 3.37 (2H, t, J=6.6 Hz), 3.72 (3H, s), 3.74 (3H, s), 7.70–9.35 (4H, m).

IR (KBr) ν: 2925, 2860, 2400, 2120, 1980, 1760, 1615, 1470, 1430, 1380, 1295, 1250, 1190, 1110, 1080, 1050, 1010, 740 cm$^{-1}$.

EXAMPLE A-20

2,3-Dimethoxy-6-(10-hydroxydecyl)-5-methyl-4-(N-methyl-1,4-dihydropyridin-3-ylcarbonyloxy)phenol 2,3-Dimethoxy-6-(10-hydroxydecyl)-5-methyl-4 -nicotinoyloxyphenol (1.1 g) was dissolved in dimethylformamide (5 ml). Iodomethane (0.3 ml) was added, and the mixture was allowed to react at room temperature for 16 hours. After concentration under reduced pressure, the residue was dissolved in ethyl acetate (20 ml). Water (20 ml) containing sodium hydrosulfite (1.74 g) and sodium bicarbonate (1.26 g) was added, and the mixture was stirred at room temperature for 1 hour. The organic layer was concentrated under reduced pressure, and the residue was subjected to column chromatography on silica gel and eluted with ethyl acetate to obtain the desired compound (1.1 g) as an oil.

Elemental Analysis for $C_{26}H_{39}NO_6 \cdot 0.5H_2O$ Calcd.: C,66.36; H,8.57; N,2.98 Found: C,66.40; H,8.87; N,3.04

NMR (CDCl$_3$) δ (ppm): 1.30–1.53 (16H, m), 2.03 (3H, s), 2.30 (3H, s), 2.59 (2H, t, J=8.4 Hz), 3.24 (2H, t, J=1.6 Hz), 3.63 (2H, t, J=6.5 Hz), 3.81 (3H, s), 3.91 (3H, s), 4.85 (1H, m), 5.69 (1H, dd, J=1.6,8 Hz), 7.24 (1H, d, J=1.6 Hz).

IR (KBr) ν: 2910, 2850, 1730, 1700, 1670, 1590, 1460, 1420, 1370, 1280, 1250, 1170, 1095, 1030, 715 cm$^{-1}$.

EXAMPLE A-21

2,3-Dimethoxy-4-hydroxy-6-(10-hydroxydecyl)-5-methyl-1-(N-methyl-1,4-dihydropyridin-3-ylcarbonyloxy)benzene A mixture of 4-tert-butyldiphenylsilyloxy-2,3-dimethoxy-6-(10-tirityloxydecyl)-5-methylphenol (4 g) obtained in Example B-3, nicotinoyl chloride hydrochloride (1 g), triethylamine (1.5 g) and dichloromethane (20 ml) was allowed to react at room temperature for 16 hours. Then methanol (50 ml) and conc. hydrochloric acid (3 ml) were added to the reaction mixture, and the mixture was heated under reflux for 30 minutes. The reaction mixture was concentrated under reduced pressure, and the residue was dissolved in ethyl acetate and washed with an aqueous solution of sodium bicarbonate. The organic layer was concentrated under reduced pressure, and the residue was dissolved in tetrahydrofuran (30 ml). Tetrabutylammonium fluoride trihydrate (1.2 g) was added, and the mixture was stirred at room temperature for 1 hour. The solvent was distilled off under reduced pressure. The residue was dissolved in dimethylformamide (5 ml), and iodomethane (0.6 ml) was added followed by reaction at room temperature for 16 hours. After concentration under reduced pressure, the residue was dissolved in ethyl acetate (30 ml). Water (30 ml) containing sodium hydrosulfite (3.5 g) and sodium bicarbonate (2.5 g) was added, and the mixture was stirred at room temperature for 1 hour. The organic layer was concentrated under reduced pressure. The residue was subjected to column chromatography on silica gel and eluted with ethyl acetate/hexane (1:1) to obtain the desired compound (1.0 g) as an oil.

Elemental Analysis for $C_{26}H_{39}NO_6 \cdot 0.5H_2O$ Calcd.: C,66.36; H,8.57; N,2.98 Found: C,66.34; H,9.02; N,2.89

NMR (CDCl$_3$) δ (ppm): 1.26–1.55 (16H, m), 2.16 (3H, s), 2.43 (2H, m), 2.99 (3H, s), 3.24 (2H, br.s), 3.64 (2H, t, J=6.5 Hz), 3.81 (3H, s), 3.92 (3H, s), 4.86 (1H, m), 5.65–5.80 (1H, m), 7.24 (1H, d, J=1.4 Hz).

IR (KBr) ν: 3400, 2910, 2850, 1730, 1700, 1670, 1580, 1460, 1420, 1380, 1315, 1260, 1160, 1100, 1040, 715 cm$^{-1}$.

EXAMPLE B-5

4-tert-Butyldiphenylsilyloxy-1-hydroxy-6-(6-methoxycarbonyl-1-phenylhexyl)-2,3,5-trimethylbenzene 6-(6-Carboxy-1-phenylhexyl)-2,3,5 -trimethylbenzoquinone (29 g) was suspended in ether (500 ml). Diazomethane/ether solution was added until the raw material was disappeared on thin-layer chromatography. Then the ether layer was washed with water, dried over anhydrous sodium sulfate and concentrated. The concentrate was subjected to short column chromatography using silica gel (500 ml) and eluted with hexane/dichloromethane (1:1) to obtain 6-(6-methoxycarbonyl-1-phenylhexyl)-2,3,5 -trimethylbenzoquinone (25.5 g) as an orange oil. This oil was dissolved in ether (200 ml) and stirred at room temperature for 1.5 hours with a solution containing sodium hydrosulfite (52 g) in water (200 ml). The ether layer was separated and washed with saturated brine, dried over anhydrous sodium sulfate and concentrated to obtain 6-(6-methoxycarbonyl-1 -phenylhexyl)-2,3,5-trimethylhydroquinone (25.5 g). Then this compound was dissolved in dichloromethane (35 ml), imidazole (9.37 g, 2 eq.) was added, tert-butyldiphenylsilyl chloride (28.36 g, 1.5 eq.) was added dropwise with stirring at room temperature and the mixture was allowed to react overnight. The deposited imidazole hydrochloride was filtered off, and the filtrate was concentrated. The concentrate was subjected to column chromatography on silica gel (800 ml) and eluted with dichloromethane/hexane (2:1) to obtain the desired compound as a pale yellow viscous oil (46 g).

Elemental Analysis for $C_{39}H_{48}O_4Si$ Calcd.: C,76.93; H, 7.95 Found: C,76.97; H, 8.14

NMR (CDCl$_3$) δ (ppm): 1.04–2.29 (10H, m), 1.13 (9H, s), 1.96 (6H, s), 2.03 (3H, s), 3.64 (3H, s), 4.21 (1H, t, J=7 Hz), 7.14–7.74 (15H, m).

IR (film) ν: 3530, 1740 cm$^{-1}$.

EXAMPLE A-22

Monosodium
6-(6-carboxy-1-phenylhexyl)-4-hydroxy-2,3,5-trimethylphenyl-1-sulfate
monotetra-n-butylammonium salt 4-tert-Butyldiphenylsilyloxy-1-hydroxy-6-(6-methoxycarbonyl-1-phenylhexyl)-2,3,5-trimethylbenzene (660 mg, 1.08 mM) was dissolved in dimethylformamide (5 ml). Sulfur trioxide pyridine complex (650 mg, 4.08 mM) was added, and the mixture was allowed to react at room temperature for 2 days. The reaction mixture was added to a mixture of methanol (20 ml) and 2N sodium hydroxide solution (8 ml) under ice-cooling with stirring, and then the mixture was allowed to react at room temperature for 2 hours. The mixture was stirred for 30 minutes while adding dry ice powder (20 g) little by little. The reaction mixture was concentrated to dryness, and tetrahydrofuran (30 ml), water (5 ml) and tetra-n-butylammonium fluoride trihydrate (630 mg, 2.0 mM) were added to the residue. Then the mixture was allowed to react at room temperature for 2 hours. The reaction mixture was concentrated to dryness. The residue was subjected to MCI gel (trade mark) CHP-20P column chromatography eluting with 70% methanol and then Sephadex (trade mark) LH-20 column chromatography eluting with water and lyophilized to obtain the desired compound as colorless powder (59 mg).

mp: 130°–139° C.

Elemental Analysis for $C_{38}H_{62}NO_7SNa\cdot4.1H_2O$ Calcd.: C,58.98; H, 9.14; N,1.81 Found: C,58.80; H, 8.97; N,1.53

NMR (CD$_3$OD) δ (ppm): 1.01 (9H, t, J=7 Hz), 1.30–2.15 (22H, m), 1.69 (3H, s), 2.15 (3H, s), 2.35 (3H, s), 3.17–3.33 (6H, m), 5.16 (1H, t, J=8 Hz), 7.00–7.34 (5H, m).

IR (KBr) ν: 3420, 1570, 1250 cm$^{-1}$.

EXAMPLE A-23

Monosodium 6-(6-carboxy-1-phenylhexyl)-4-hydroxy-2,3,5-trimethylphenyl-1-sulfate Monosodium 6-(6-carboxy-1-phenylhexyl)-4-hydroxy-2,3,5-trimethylphenyl-1-sulfate monotetra-n-butylammonium salt (30 mg, 0.0429 mM) was dissolved in water (15 ml). The solution was subjected to strong acid type ion exchange resin (manufactured by Bio-Rad, AG50W-X8, 100–200 mesh; Na type) column (φ 3×7 cm) and eluted with water (200 ml). The desired fraction was concentrated. The residue was subjected to Sephadex (trade mark) LH-20 column chromatography, eluted with water and lyophilized to obtain the desired compound as colorless powder (16 mg).

mp: 195°–199° C.

Elemental Analysis for $C_{22}H_{26}O_7SNa\cdot3.8H_2O$ Calcd.: C,50.14; H, 6.62; S,6.08 Found: C,49.94; H, 6.50; S,6.08

NMR (CD$_3$OD) δ (ppm): 1.10–2.29 (8H, m), 1.69 (3H, s), 2.15 (3H, s), 2.34 (3H, s), 5.16 (1H, t, J=SHz), 7.00–7.33 (5H, m).

IR (KBr) ν: 3440, 1615, 1560, 1240 cm$^{-1}$.

EXAMPLE A-24

Disodium 6-(6-carboxy-1-phenylhexyl)-4-hydroxy-2,3,5-trimethylphenyl-1-O-β-D-glucopyranosiduronate 4-tert-Butyldiphenylsilyloxy-1-hydroxy-6-(6-methoxycarbonyl-1-phenylhexyl)-2,3,5-trimethylbenzene (881 mg, 1.447 mM) and methyl 1-imino-2-trichloroethyl-O-α-D-2', 3',4'-triacetylglucopyranosiduronate (1.01 g, 2.11 mM) were dissolved in dichloromethane (5 ml). Boron trifluoride ether complex (0.25 ml, 1.95 mM) was added with stirring under ice-cooling, and the mixture was allowed to react at room temperature for 2 days. The reaction mixture was poured into ice-cooled water (20 ml) and extracted with dichloromethane (10 ml) twice. The extract was subjected to column chromatography on silica gel and eluted with hexane/ethyl acetate (4:1) to obtain a pale yellow waxy material (636 mg). The material (610 mg) was dissolved in tetrahydrofuran (10 ml), and a solution of tetra-n-butylammonium fluoride trihydrate (0.26 g, 0.82 mM) in tetrahydrofuran (3 ml) was added. The mixture was allowed to react for 15 minutes. Methanol (15 ml) and 2N sodium hydroxide solution (2.5 ml) were added, and the mixture was stirred for additional 2 hours at room temperature. The reaction mixture was adjusted to pH 4.5 with 6N hydrochloric acid followed by adjustment to pH 8.5 with sodium bicarbonate, and the solvent was distilled off by concentration under reduced pressure. The concentrate was subjected to Sephadex (trade mark) LH-20 column chromatography and eluted with water. The desired fraction was lyophilized to obtain the desired compound as white powder (75 mg).

mp: 204°–205° C. (dec.)

Elemental Analysis for $C_{28}H_{34}O_{10}Na_2 5H_2O$ Calcd.: C,50.45; H, 6.65 Found: C,50.70; H, 6.63

NMR (CD$_3$OD) δ (ppm): 1.10–2.25 (10H, m), 1.70 and 1.78 (each 1.5H, s), 2.12 and 2.15 (each 1.5H, s), 2.29 and 2.33 (each 1.5H, s), 3.01–3.61 (4H, m), 4.45 and 4.67 (each 0.5H, d, J=8 Hz), 5.08 (1H, t, J=8 Hz), 6.98–7.30 (5H, m).

IR (KBr) ν: 3400, 1610, 1560, 1410, 1060 cm$^{-1}$.

EXAMPLE A-25

1-Acetoxy-4-hydroxy-6-(6-methoxycarbonyl-1-phenylhexyl)-2,3,5-trimethylbenzene 4-tert-Butyldiphenylsilyloxy-1-hydroxy-6-(6-methoxycarbonyl-1-phenylhexyl)-2,3,5-trimethylbenzene (22.2 g, 36.46 mM) was dissolved in dichloromethane (200 ml) and triethylamine (8.3 ml, 59.9 mM). Acetyl chloride (4.1 ml, 57.7 mM) was added under ice-cooling, and the mixture was stirred for 2 hours. The reaction mixture was poured into ice-cooled water (100 ml) and stirred for 20 minutes. Then the organic layer was washed with water, dried over anhydrous sodium sulfate and concentrated to obtain 1-acetoxy-4-tert-butyldiphenylsilyloxy-6-(6-methoxycarbonyl-1-phenylhexyl)-2,3,5-trimethylbenzene as a pale yellow oil. This oil was dissolved in tetrahydrofuran (70 ml). 1M tetra-n-butylammonium fluoride trihydrate/tetrahydrofuran solution (73 ml) was added, and the mixture was stirred at room temperature for 1 hour. The reaction mixture was poured into ice-cooled water (150 ml) and extracted with ethyl acetate (150 ml). The organic layer was washed with water followed by saturated brine and dried over anhydrous sodium sulfate. The solvent was distilled off under reduced pressure, and the residue was recrystallized from hexane to obtain the desired compound as pale yellow prisms (9.03 g).

mp: 146°–148° C.

Elemental Analysis for $C_{25}H_{32}O_5$ Calcd.: C,72.79; H, 7.82 Found : C,72.80; H, 7.52

NMR (CDCl$_3$) δ (ppm): 1.15–2.10 (8H, m), 1.94 (3H, s), 2.02 (3H, s), 2.17 (3H, s), 2.25 (3H, s), 2.28 (2H, t, J=8 Hz), 3.66 (3H, s), 4.35 (1H, br.s), 4.62 (1H, br.s), 7.10–7.22 (5H, m).

IR (KBr) ν: 2480, 1750, 1740, 1210 cm$^{-1}$.

EXAMPLE A-26

Monosodium 6-(6-carboxy-1-phenylhexyl)-1-hydroxy-2,3,5-trimethylphenyl-4-sulfate 1-Acetoxy-4-hydroxy-6-(6-methoxycarbonyl-1-phenylhexyl)-2,3,5-trimethylbenzene (308 mg, 0.747 mM) and sulfur trioxide triethylamine complex (700 mg, 5.0 mM) were stirred in dimethylformamide (5 ml) at room temperature for 15 hours and then at 43° C. for 5 hours. The reaction mixture was added to a mixture of 2N aqueous sodium hydroxide solution (10 ml) and methanol (20 ml) under ice-cooling, and the resulting mixture was stirred at room temperature for 4 hours. The reaction mixture was neutralized with 6N hydrochloric acid and concentrated to dryness. The residue was subjected to Sephadex (trade mark) LH-20 column chromatography and eluted with water. The desired fraction was concentrated and lyophilized to obtain the desired compound as white powder (284 mg).

mp: 160°–164° C.

Elemental Analysis for $C_{22}H_{27}O_7SNa \cdot 3.3H_2O$ Calcd.: C,51.02; H, 6.54 Found: C,51.04; H, 6.28

NMR (CD$_3$OD) δ (ppm): 1.15–2.30 (10H, m), 2.09 (3H, s), 2.28 (3H, s), 2.59 (3H, s), 4.54 (1H, br.s), 7.02–7.29 (5H, m).

IR (KBr) ν: 3500, 1560, 1410, 1230 cm$^{-1}$.

EXAMPLE A-27

Disodium 6-(6-carboxy-1-phenylhexyl)-1-hydroxy-2,3,5-trimethylphenyl-4-O-β-D-glucopyranosiduronate 1-Acetoxy-4-hydroxy-6-(6-methoxycarbonyl-1-phenylhexyl)-2,3,5-trimethylbenzene (300 mg, 0.727 mM) and methyl 1-imino-2-trichloroethyl-O-α-D-2',3',4'-triacetylglucopyranosiduronate (600 mg, 1.25 mM) were dissolved in dichloromethane (5 ml). Boron trifluoride ether complex (0.12 ml, 0.96 mM) was added with stirring under ice-cooling, and the mixture was allowed to react for 5 hours. The reaction mixture was poured into ice-cooled water (30 ml) and extracted with ethyl acetate (30 ml). The extract was concentrated and dissolved in methanol (30 ml). 1N sodium hydroxide solution (7 ml) was added with stirring under ice-cooling, and the mixture was allowed to react at room temperature for 2 hours. The reaction mixture was adjusted to pH 6 with 6N hydrochloric acid followed by adjustment to pH 7.9 with sodium bicarbonate and concentrated. The concentrate was subjected to Sephadex (trade mark) LH-20 column chromatography eluting with water and lyophilized to obtain the desired compound as colorless powder (210 mg).

mp: 215°–220° C.

Elemental Analysis for $C_{28}H_{34}O_{10}Na_2 \cdot 4H_2O$ Calcd.: C,51.85; H, 6.53 Found : C,52.03; H, 6.69

NMR (CD$_3$OD) δ (ppm); 1.20–2.30 (10H, m), 2.07 (3H, s) , 2.26 (6H, s), 3.38–3.61 (4H, m), 4.53 (1H, d, J=7 Hz), 7.01–7.28 (5H, m).

IR (KBr) ν: 3430, 1610, 1560, 1410 cm$^{-1}$.

What is claimed is:

1. A compound of the formula

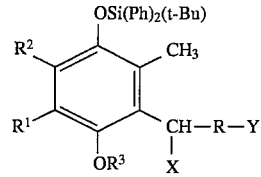

wherein $R^1$ and $R^2$ are the same or different and are methyl or methoxy, or $R^1$ and $R^2$ are joined together to form the group of the formula: —CH=CH—CH=CH—;

$R^3$ is hydrogen or a protecting group selected from the group consisting of acetyl, propionyl, butyryl, benzoyl, nicotinoyl, tetrahydropyranyl, methoxymethyl, ethoxyethyl, methoxyethoxymethyl, methylthiomethyl and trityl;

X is thienyl unsubstituted or substituted by at least one substituent selected from the group consisting of alkyl of 1–3 carbon atoms, alkoxy of 1–3 carbon atoms and halogen;

R is a saturated or unsaturated bivalent straight-chain hydrocarbon group having up to 20 carbon atoms or a chemical bond;

Y is a member selected from the group consisting of
  (1) hydrogen,
  (2) hydroxymethyl,
  (3) methoxymethyloxymethyl,
  (4) acetoxymethyl,
  (5) nitroxymethyl,
  (6) aminocarbonyloxymethyl,
  (7) methylaminocarbonyloxymethyl,
  (8) ethylaminocarbonyloxymethyl,
  (9) dimethylaminocarbonyloxymethyl,
  (10) phenylaminocarbonyloxymethyl,
  (11) morpholinocarbonyloxymethyl
  (12) piperidinocarbonyloxymethyl,
  (13) carboxyl,
  (14) alkoxycarbonyl having 2 to 5 carbon atoms,
  (15) aryloxycarbonyl having 7 to 8 carbon atoms, and
  (16) aminocarbonyl which is unsubstituted or is substituted by
    (a) hydroxyl,
    (b) alkyl of 1 to 4 carbon atoms,
    (c) phenyl or naphthyl each of which is unsubstituted or is substituted by hydroxyl, amino, nitro, halogen, methyl or methoxy,
    (d) morpholinocarbonyl,
    (e) thiomorpholinocarbonyl, or
    (f) piperidinocarbonyl;

Ph is phenyl; and
t-Bu is tert-butyl.

2. A compound according to claim 1, wherein Y is
  (1) hydroxymethyl,
  (2) carboxyl,
  (3) alkoxycarbonyl having 2 to 5 carbon atoms,
  (4) aryloxycarbonyl having 7 to 8 carbon atoms, or
  (5) aminocarbonyl which is unsubstituted or is substituted by (a) hydroxyl,
(b) alkyl having 1 to 4 carbon atoms,
(c) phenyl or naphthyl each of which is unsubstituted or is substituted by hydroxyl, amino, nitro, halogen, methyl or methoxy,
(d) morpholinocarbonyl,
(e) thiomorpholinocarbonyl, or
(f) piperidinocarbonyl.

3. A compound according to claim 1 wherein $R^1$ and $R^2$ are independently methyl or methoxy.

4. A compound according to claim 1 wherein R is a saturated or unsaturated bivalent straight-chain hydrocarbon group of 5 to 8 carbon atoms,

* * * * *